US011497263B1

(12) United States Patent
Deshaies et al.

(10) Patent No.: US 11,497,263 B1
(45) Date of Patent: Nov. 15, 2022

(54) GARMENTS WITH MOISTURE CAPTURE ASSEMBLIES AND ASSOCIATED METHODS

(71) Applicant: Knix Wear Inc., Toronto (CA)

(72) Inventors: Lyne Deshaies, Toronto (CA); Talia Greenberg, Toronto (CA); Joanna Griffiths, Toronto (CA); Steven Hudson, Toronto (CA); Jeremy Jiang, Kunshan (CN); Julie Power, Toronto (CA); Linda Kritikos, Toronto (CA)

(73) Assignee: Knix Wear Inc., Toronto (CA)

( * ) Notice: Subject to any disclaimer, the term of this patent is extended or adjusted under 35 U.S.C. 154(b) by 0 days.

(21) Appl. No.: 17/717,986

(22) Filed: Apr. 11, 2022

Related U.S. Application Data

(60) Provisional application No. 63/273,429, filed on Oct. 29, 2021, provisional application No. 63/219,763, filed on Jul. 8, 2021.

(51) Int. Cl.
*A41D 31/12* (2019.01)
(52) U.S. Cl.
CPC ................... *A41D 31/125* (2019.02)
(58) Field of Classification Search
CPC .......... A41D 31/125; A61F 13/00029
USPC .......................................................... 604/385
See application file for complete search history.

(56) References Cited

U.S. PATENT DOCUMENTS

| 3,608,551 A | 9/1971 | Saburo |
| 4,044,769 A | 8/1977 | Papajohn |
| 4,355,425 A | 10/1982 | Jones et al. |
| 4,560,381 A | 12/1985 | Southwell |
| 4,781,962 A | 11/1988 | Zamarripa et al. |
| 4,847,134 A | 7/1989 | Fahrenkrug et al. |
| 5,151,092 A | 9/1992 | Buell et al. |
| 5,167,897 A | 12/1992 | Weber et al. |
| 5,217,782 A | 6/1993 | Moretz et al. |
| 5,308,346 A | 5/1994 | Sneller et al. |
| 5,342,338 A | 8/1994 | Roe |
| 5,360,420 A | 11/1994 | Cook et al. |

(Continued)

FOREIGN PATENT DOCUMENTS

| AU | 2014218471 B2 | 10/2016 |
| CA | 2126280 | 12/1994 |

(Continued)

OTHER PUBLICATIONS

English-language machine translation of Japan Patent Application Publication No. JP2005154922, Jun. 16, 2005.

(Continued)

*Primary Examiner* — Khaled Annis
(74) *Attorney, Agent, or Firm* — Kolitch Romano Dascenzo Gates LLC

(57) ABSTRACT

Garments comprise a plurality of adhesive bonds within a bonded region of the garment; a garment base that defines a garment lateral edge; and a moisture capture assembly bonded to the garment base within the bonded region. The moisture capture assembly comprises a moisture retention portion configured to absorb and retain moisture; and an anti-leak portion configured to restrict moisture from exiting the moisture retention portion. The bonded region extends fully around a perimeter of the moisture capture assembly, and the moisture capture assembly and the bonded region do not extend to the garment lateral edge.

18 Claims, 11 Drawing Sheets

(56) References Cited

U.S. PATENT DOCUMENTS

| | | | |
|---|---|---|---|
| 5,368,910 | A | 11/1994 | Langdon |
| 5,411,498 | A | 5/1995 | Fahrenkrug et al. |
| 5,449,352 | A | 9/1995 | Nishino et al. |
| 5,500,270 | A | 3/1996 | Langdon et al. |
| 5,507,895 | A | 4/1996 | Suekane |
| 5,518,801 | A | 5/1996 | Chappell et al. |
| 5,665,452 | A | 9/1997 | Langdon et al. |
| 5,677,028 | A | 10/1997 | Ravella |
| 5,693,169 | A | 12/1997 | Langdon et al. |
| H1732 | H | 6/1998 | Johnson |
| H1746 | H | 8/1998 | Carrier et al. |
| 5,851,204 | A | 12/1998 | Mizutani |
| 5,879,487 | A | 3/1999 | Ravella |
| 5,899,895 | A | 5/1999 | Robles et al. |
| 6,117,523 | A | 9/2000 | Sugahara |
| 6,120,487 | A | 9/2000 | Ashton |
| 6,174,303 | B1 | 1/2001 | Suprise et al. |
| 6,231,554 | B1 | 5/2001 | Menard |
| 6,240,569 | B1 | 6/2001 | Van Gompel et al. |
| 6,355,330 | B1 | 3/2002 | Koslow et al. |
| 6,381,994 | B1 | 5/2002 | Lee |
| 6,610,901 | B2 | 8/2003 | McMahon-Ayerst et al. |
| 6,622,312 | B2 | 9/2003 | Rabinowicz |
| 6,861,520 | B1 | 3/2005 | Todd et al. |
| 7,008,887 | B2 | 3/2006 | Rearick et al. |
| 7,083,604 | B2 | 8/2006 | Sakaguchi |
| 7,156,828 | B2 | 1/2007 | Ostrow |
| RE39,919 | E | 11/2007 | Dodge, II et al. |
| 7,322,966 | B1 | 1/2008 | Deerin |
| 7,951,128 | B1 | 5/2011 | Lewis |
| 8,058,343 | B2 | 11/2011 | Liu et al. |
| 8,117,675 | B2 | 2/2012 | Strange et al. |
| 8,460,265 | B1 | 6/2013 | Calender |
| D716,020 | S | 10/2014 | Dunbar et al. |
| 10,226,388 | B2 * | 3/2019 | Nelson ............... A61F 13/51464 |
| 10,335,325 | B2 * | 7/2019 | Sheldon ............... A61G 17/042 |
| 10,441,479 | B2 | 10/2019 | Griffiths |
| 10,441,480 | B2 | 10/2019 | Griffiths |
| 10,765,564 | B2 * | 9/2020 | Lee ................... A61F 13/47218 |
| 10,905,596 | B2 * | 2/2021 | Sina ................... A61F 13/15699 |
| 11,331,229 | B2 * | 5/2022 | Lee ................... A61F 13/49011 |
| 2001/0031957 | A1 * | 10/2001 | Prestley ................. A61F 13/539 |
| | | | 604/385.25 |
| 2002/0177829 | A1 * | 11/2002 | Fell ....................... A61F 13/539 |
| | | | 604/385.01 |
| 2003/0004488 | A1 | 1/2003 | Ashton et al. |
| 2003/0124927 | A1 | 7/2003 | Waldroup et al. |
| 2003/0143376 | A1 | 7/2003 | Toyoshima et al. |
| 2004/0229008 | A1 | 11/2004 | Hoying |
| 2004/0265533 | A1 | 12/2004 | Hoying et al. |
| 2005/0055002 | A1 | 3/2005 | Whitelaw et al. |
| 2005/0090790 | A1 * | 4/2005 | Veith ................... A61F 13/4915 |
| | | | 604/385.01 |
| 2005/0131365 | A1 | 6/2005 | Sakaguchi |
| 2006/0070163 | A1 | 4/2006 | Beck et al. |
| 2008/0108962 | A1 | 5/2008 | Furuta et al. |
| 2008/0275415 | A1 | 11/2008 | Wheeler et al. |
| 2008/0276352 | A1 | 11/2008 | Strange et al. |
| 2009/0240224 | A1 | 9/2009 | Underhill et al. |
| 2009/0247977 | A1 | 10/2009 | Takeuchi et al. |
| 2010/0222759 | A1 | 9/2010 | Hammons et al. |
| 2010/0249736 | A1 | 9/2010 | Png et al. |
| 2011/0048077 | A1 | 3/2011 | Warren et al. |
| 2013/0006209 | A1 * | 1/2013 | Ruiz ....................... A61F 13/68 |
| | | | 604/385.14 |
| 2013/0072888 | A1 | 3/2013 | Zorin |
| 2014/0039432 | A1 | 2/2014 | Dunbar et al. |
| 2014/0378935 | A1 | 12/2014 | Arayama et al. |
| 2020/0000649 | A1 | 1/2020 | Griffiths |
| 2020/0222256 | A1 | 7/2020 | Chong |
| 2022/0117790 | A1 * | 4/2022 | Locke ............... A61F 13/00059 |
| 2022/0117792 | A1 * | 4/2022 | Bradford ........... A61F 13/00029 |
| 2022/0133544 | A1 * | 5/2022 | Turton ............. A61F 13/00995 |
| | | | 604/372 |

FOREIGN PATENT DOCUMENTS

| | | |
|---|---|---|
| CA | 2126281 | 12/1994 |
| CA | 2152135 | 12/1995 |
| EP | 1370161 | 5/2006 |
| JP | 2005154922 | 6/2005 |
| JP | 2005154924 | 6/2005 |
| KR | 20070018490 | 2/2007 |
| KR | 100694187 | 3/2007 |
| WO | WO 1997046198 | 12/1997 |
| WO | WO 2006036841 | 4/2006 |

OTHER PUBLICATIONS

English-language machine translation of Japan Patent Application Publication No. JP2005154924, Jun. 16, 2005.

English-language machine translation of Korea Patent No. KR100694187, Mar. 6, 2007.

English-language machine translation of Korea Patent Application Publication No. KR20070018490, Feb. 14, 2007.

"Bemis SewFree" webpage (www.bemisheatseal.com/Sewfree.htm), 2 pages, available at least as early as Aug. 4, 2001, retrieved from Internet Archive Wayback Machine (https://web.archive.org/web/20010804041402/http://www.bemisheatseal.com:%2080/Sewfree.htm) on Jan. 29, 2021.

Lo, T.Y., "Techtextil/Avantex 2005 (2)" *Textile Asia*, 2005, pp. 26-27.

Isaacs, Mac, "Seamless: Eliminating Stitches—More Than a Buzzword," *AATCC Review*, Nov. 2005, pp. 16-19.

Swantko, Kathlyn, "Forming a New Bond," *FabricTrends: A GearTrends Supplement*, 2004, pp. 12-14.

Bemis Associates, *Sewfree Adhesive Films for Intimate Apparel*, 2013, 8 pages.

Photographs of Adidas Techfit Period-Proof Biker Short Tights, ordered Jun. 24, 2021.

Photographs Lilova Seamless High Waist, ordered Oct. 12, 2021.

Photographs Lilova Swimwear One-Piece Classic, ordered Oct. 12, 2021.

Photographs of Modibodi Seamfree Bikini Moderate-Heavy, ordered Feb. 9, 2022.

Photographs of Proof Leakproof Hipster Underwear, ordered Aug. 7, 2020.

Photographs of Pure Rosy Banded Brief—Jam, ordered Oct. 12, 2021.

Photographs of Ruby /Love Period Underwear Bikini—Pretty In Pink, ordered May 6, 2021.

Photographs of SPEAX by Thinx Hiphugger Women's Underwear—Leakproof, Breathable—M—Beige, ordered Feb. 7, 2020.

Photographs of TomboyX Leakproof Bikini—Plum, ordered Nov. 10, 2020.

* cited by examiner

GARMENTS WITH MOISTURE CAPTURE ASSEMBLIES AND ASSOCIATED METHODS

RELATED APPLICATIONS

This application claims benefit of U.S. Provisional Patent Application Nos. 63/219,763 and 63/273,429, filed on Jul. 8, 2021 and Oct. 29, 2021, respectively, the complete disclosures of which are incorporated herein by reference.

FIELD

The present disclosure relates to garments with moisture capture assemblies and associated methods.

BACKGROUND

Garments and other wearable accessories that are configured to be worn adjacent to a wearer's crotch often exhibit moisture-absorbing properties, such as to absorb and/or retain menstrual fluids and/or urine produced by the user. In particular, it generally is desirable that such garments absorb and retain such fluids in a discreet and leak-proof manner, such as to hide such fluids from view and/or to enhance the wearer's comfort. However, many such garments include absorbent regions that are bulky and thus uncomfortable and/or difficult to conceal. Moreover, many such garments utilize stitching to attach the absorbent regions to the remainder of the garment, increasing the potential for leakage through the stitching perforations and/or producing bulky seams at the expense of the wearer's comfort and the discreetness of the garment.

To address these considerations, several prior art undergarments include absorbent regions that are bonded and/or laminated to a main body portion of the undergarment. However, the arrangement of such bonds may be insufficient to fully protect against moisture exiting and/or entering the undergarment. Additionally, such constructions may be incompatible with garment applications other than traditional undergarments.

SUMMARY

Garments with moisture capture assemblies and associated methods are disclosed herein. A garment configured to be worn by a wearer includes a crotch region, a bonded region, a garment base, and a moisture capture assembly bonded to the garment base within the bonded region. Specifically, the moisture capture assembly is positioned at least partially within the crotch region. The moisture capture assembly includes an assembly interior side that faces the wearer when the garment is worn by the wearer and an assembly exterior side that faces away from the wearer when the garment is worn by the wearer. The moisture capture assembly further includes a moisture retention portion configured to absorb and retain moisture from the wearer and an anti-leak portion configured to restrict moisture from exiting the moisture retention portion. The moisture capture assembly is bonded to the garment base with a plurality of adhesive bonds formed within the bonded region. The plurality of adhesive bonds includes an internal peripheral bond positioned on an interior side of the moisture capture assembly as well as an external peripheral bond positioned on an exterior side of the moisture capture assembly.

DESCRIPTION

Figure 1:
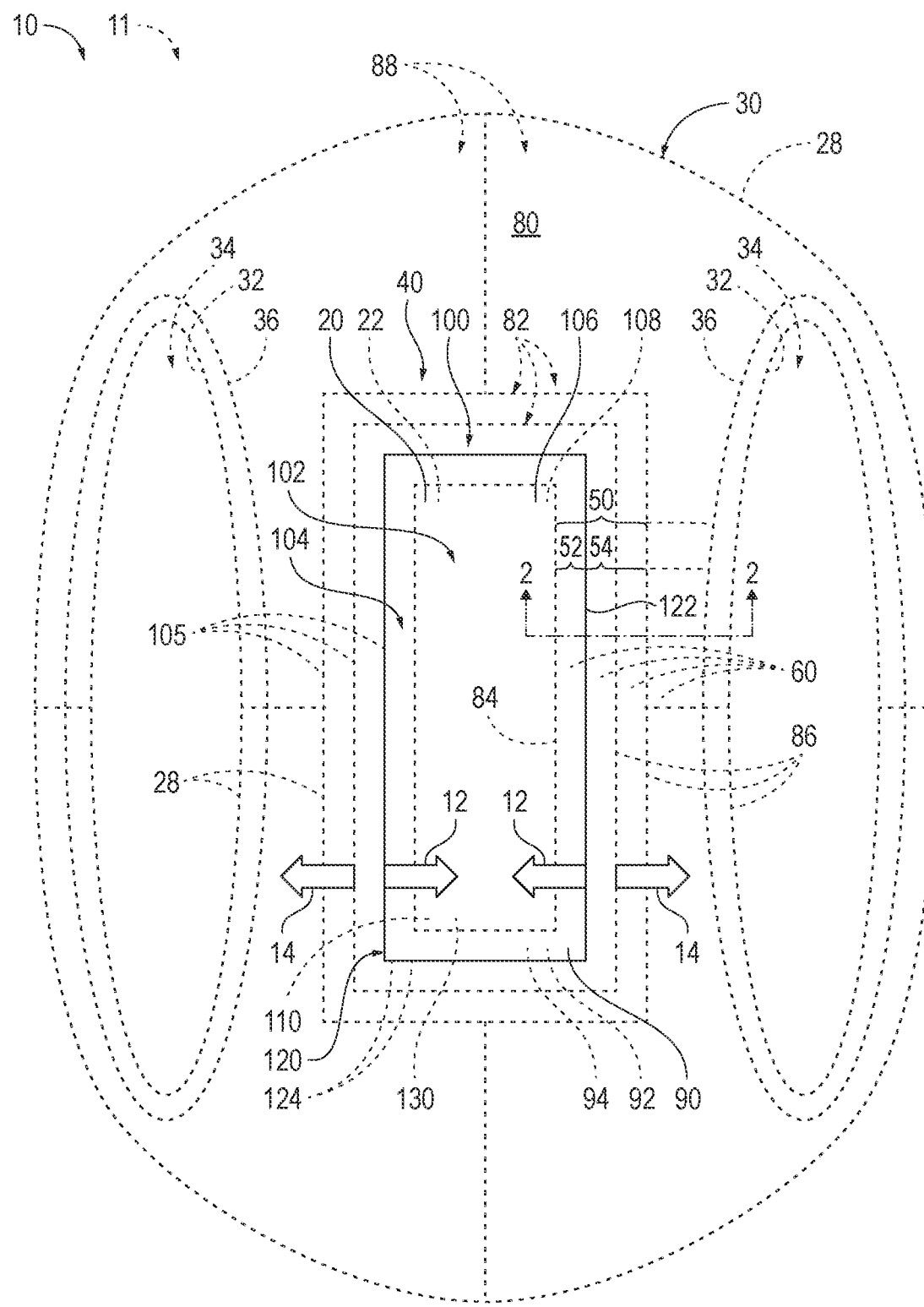
FIG. 1 is a schematic top plan view illustrating examples of garments with moisture capture assemblies according to the present disclosure.

FIGS. 1-11 provide examples of garments 10 including moisture capture assemblies 100 and/or of methods 200 of manufacturing garments 10, according to the present disclosure. Elements that serve a similar, or at least substantially similar, purpose are labeled with like numbers in each of FIGS. 1-10, and these elements may not be discussed in detail herein with reference to each of FIGS. 1-10. Similarly, all elements may not be labeled in each of FIGS. 1-11, but reference numerals associated therewith may be utilized herein for consistency. Elements, components, and/or features that are discussed herein with reference to one or more of FIGS. 1-11 may be included in and/or utilized with any of FIGS. 1-11 without departing from the scope of the present disclosure. In general, elements that are likely to be included in a particular embodiment or example are illustrated in solid lines, while elements that are optional are illustrated in dashed lines. However, elements that are shown in solid lines may not be essential and, in some embodiments or examples, may be omitted without departing from the scope of the present disclosure.

Figure 2:
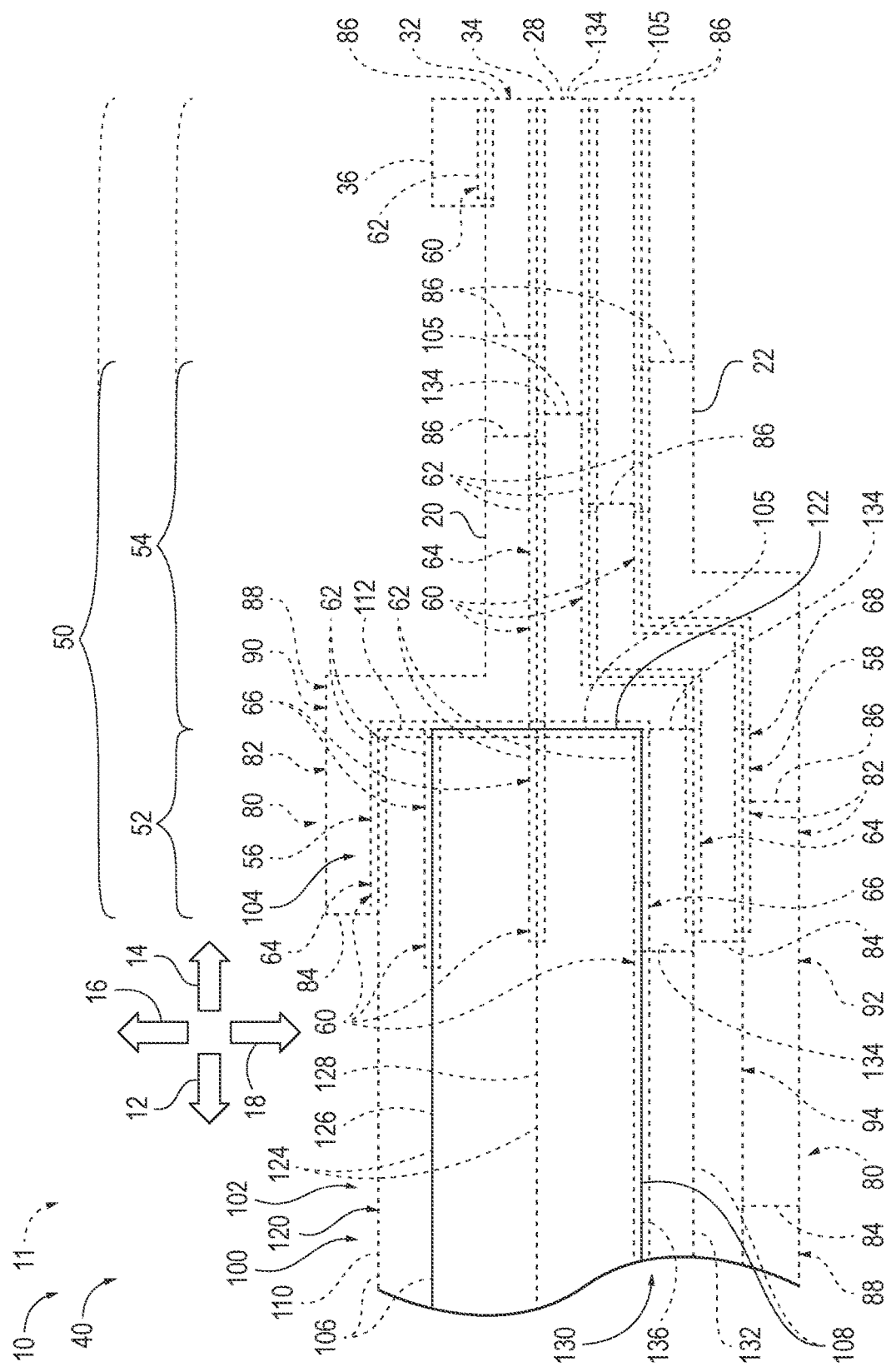
FIG. 2 is a schematic fragmentary cross-sectional side elevation view taken along the line 2-2 of FIG. 1 illustrating examples of garments with moisture capture assemblies according to the present disclosure.
Figure 3:
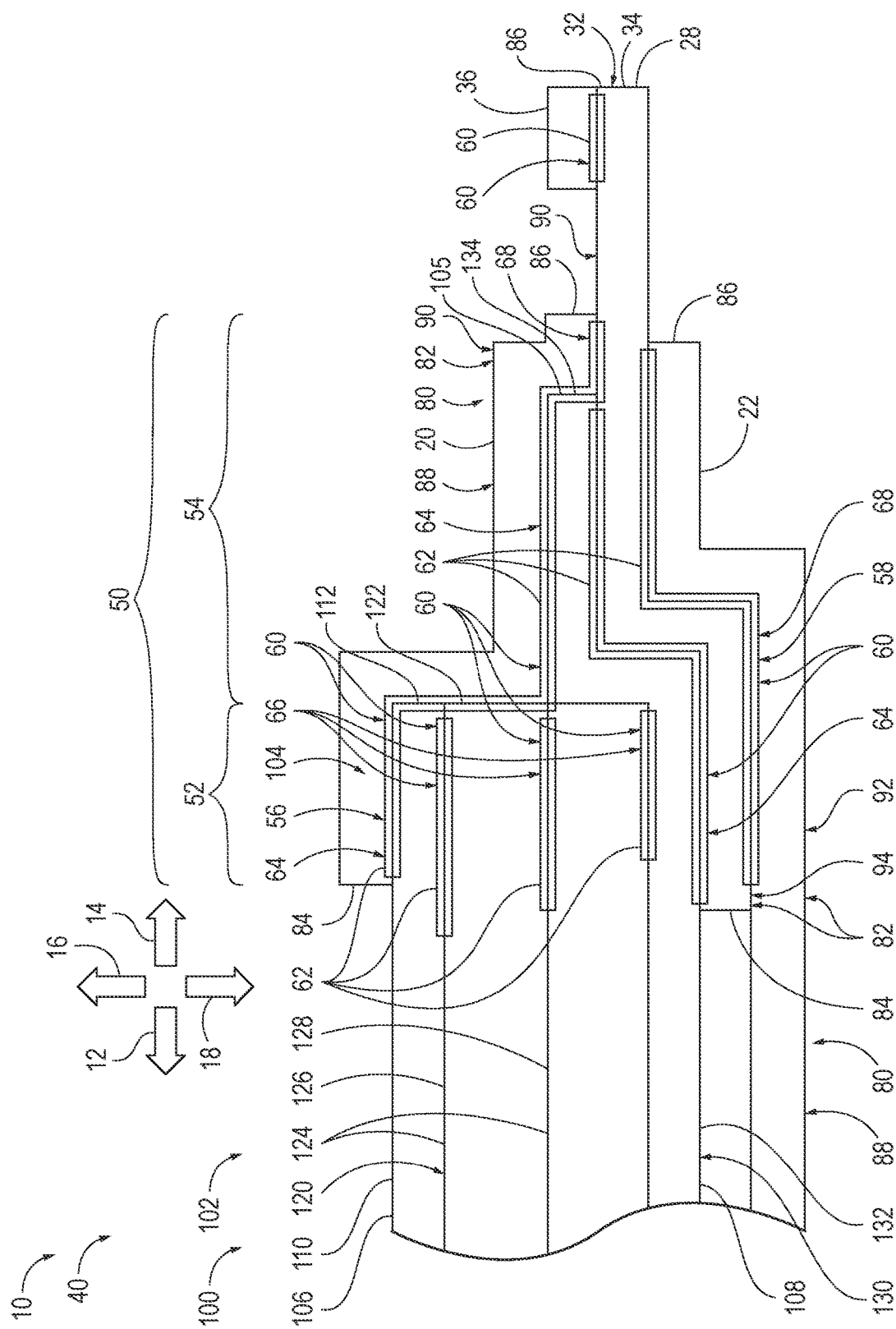
FIG. 3 is a schematic fragmentary cross-sectional side elevation view taken along the line 2-2 of FIG. 1 illustrating an example of a garment with a moisture capture assembly according to the present disclosure.
Figure 4:
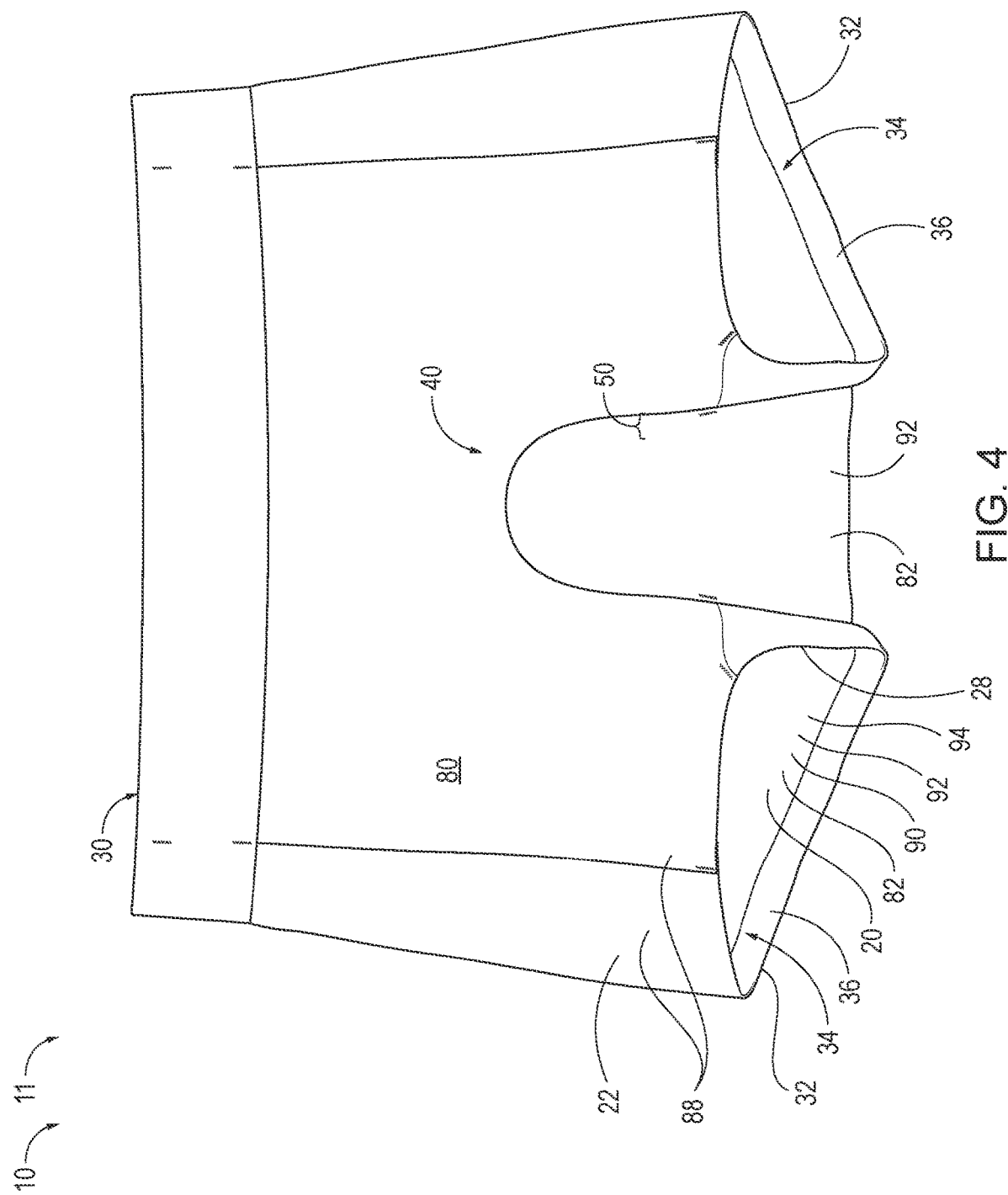
FIG. 4 is a front side elevation view illustrating an exterior of an example garment with a moisture capture assembly according to the present disclosure.
Figure 5:
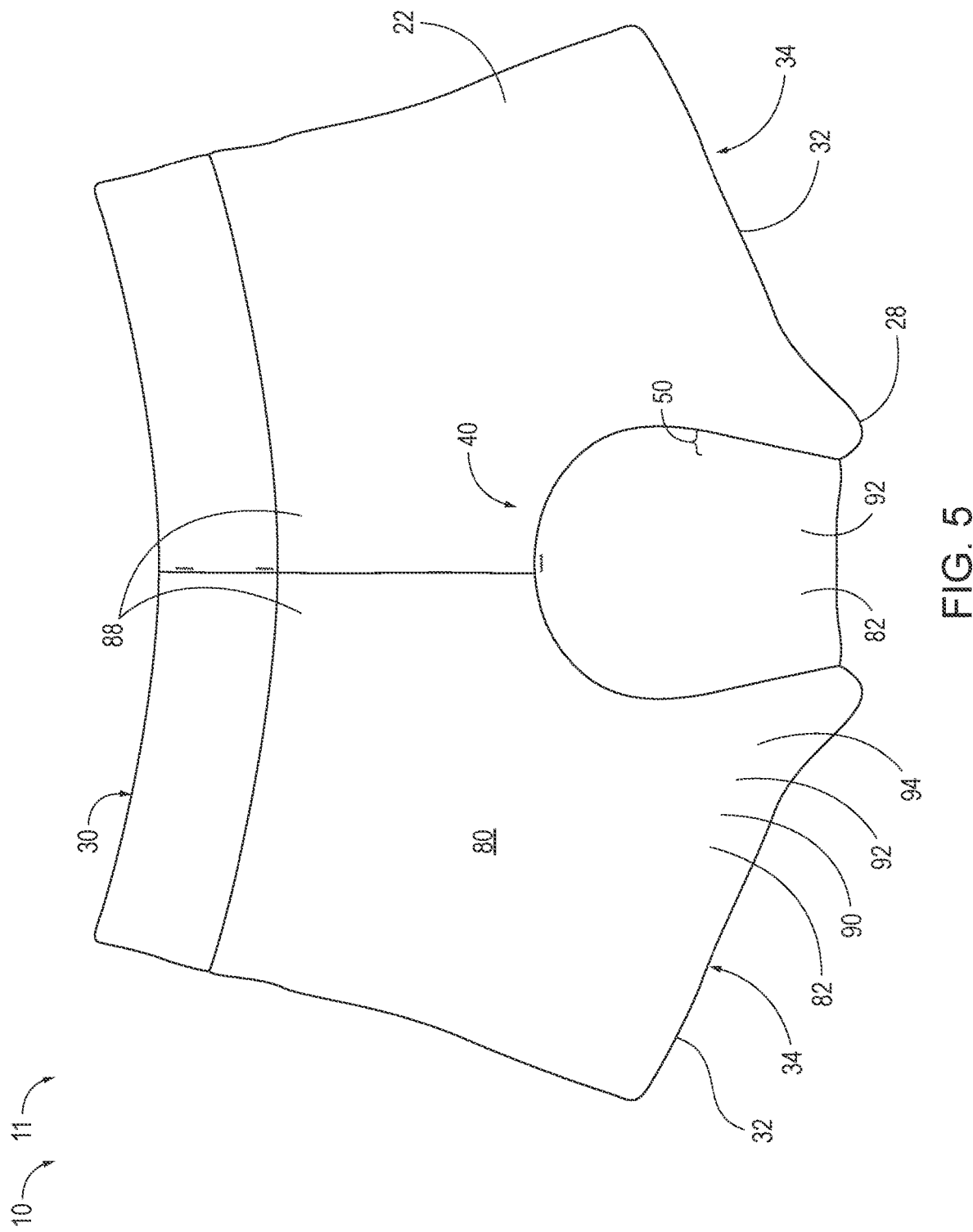
FIG. 5 is a rear side elevation view illustrating the exterior of the example garment of FIG. 4.
Figure 6:
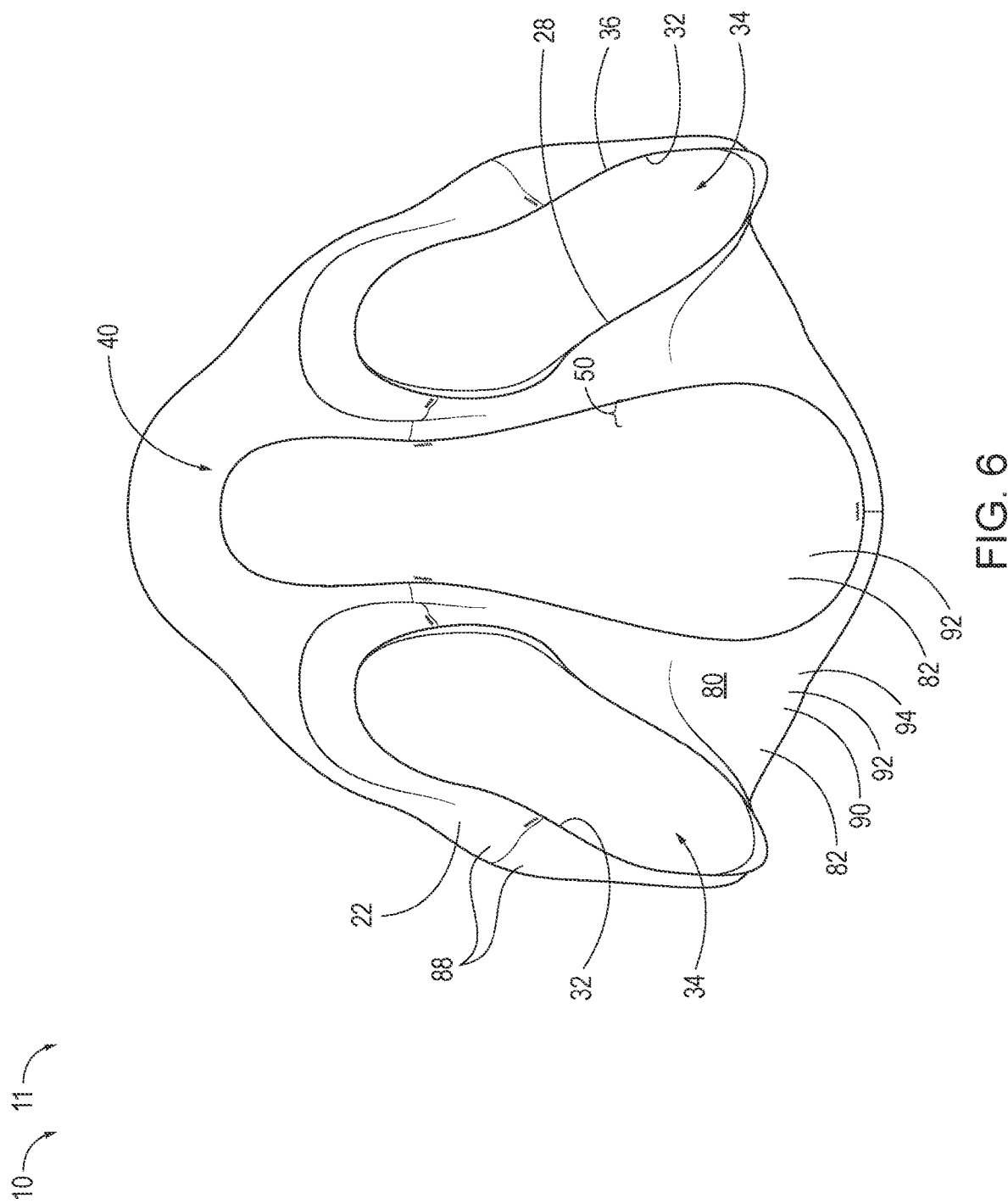
FIG. 6 is a top plan view illustrating the exterior of the example garment of FIG. 4.
Figure 7:
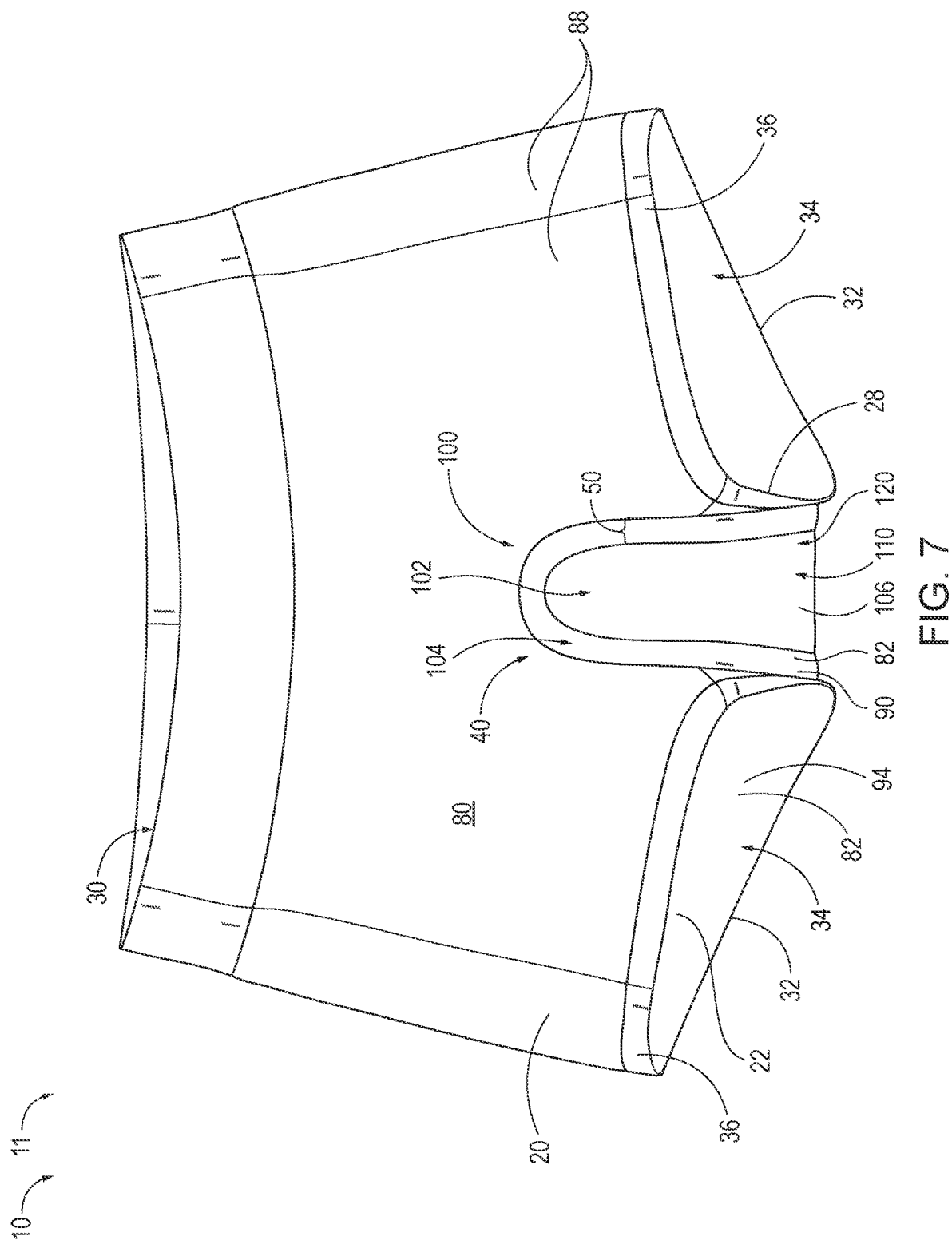
FIG. 7 is a front side elevation view illustrating an interior of the example garment of FIG. 4.
Figure 8:
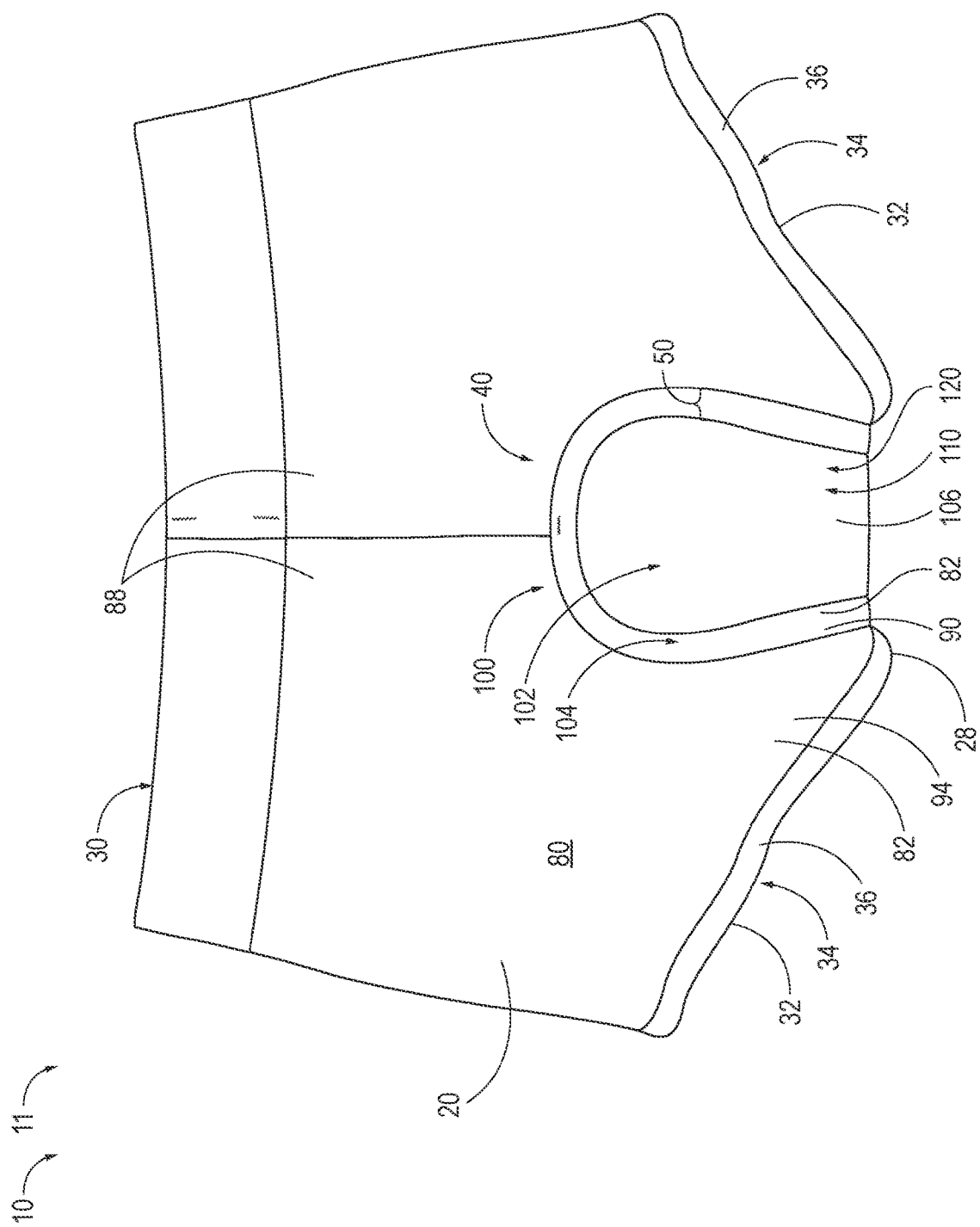
FIG. 8 is a rear side elevation view illustrating the interior of the example garment of FIG. 4.
Figure 9:
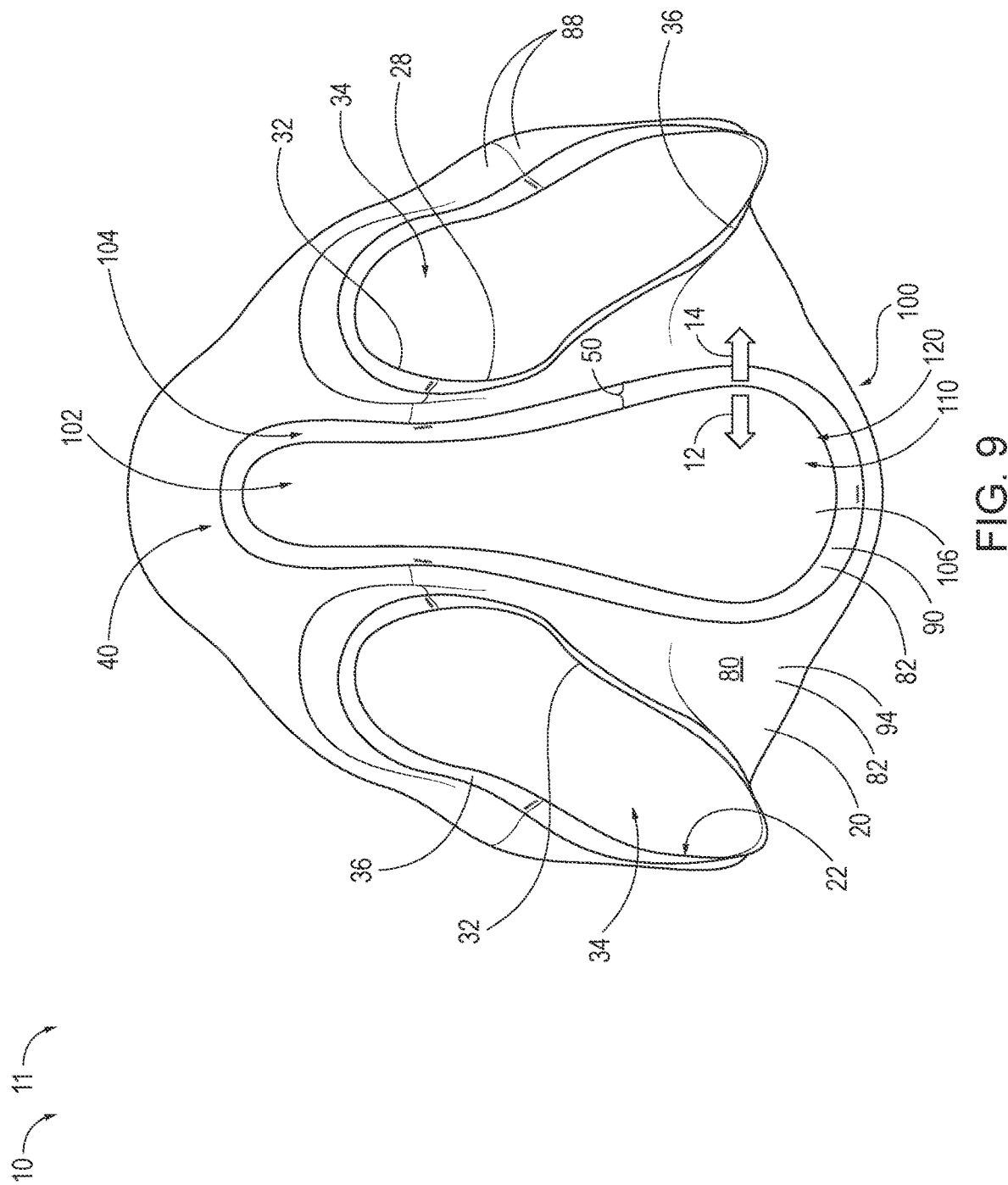
FIG. 9 is a top plan view illustrating the interior of the example garment of FIG. 4.

FIG. 1 is a schematic top plan view illustrating examples of garments 10 according to the present disclosure, while FIGS. 2-3 are schematic cross-sectional side views of garments 10 as viewed along the line 2-2 in FIG. 1. FIGS. 4-10 illustrate portions of an example garment 11, which is an example of garment 10. In particular, the schematic cross-sectional side view of FIG. 3 corresponds to the construction of example garment 11, as described in more detail herein.

As schematically illustrated in FIGS. 1-3 and less schematically illustrated in FIGS. 4-10, a garment 10 configured to be worn by a wearer includes a crotch region 40 and a bonded region 50. Garment 10 additionally includes a garment base 80 and a moisture capture assembly 100 bonded to garment base 80 within bonded region 50. As schematically illustrated in FIGS. 1-3 and less schematically illustrated in FIGS. 4-10, moisture capture assembly 100 is positioned at least partially in crotch region 40. In this manner, garment base 80 may be described as supporting moisture capture assembly 100 within crotch region 40. In particular, and as described in more detail herein, moisture capture assembly 100 is bonded to garment base 80 with a plurality of adhesive bonds 60 that are formed within bonded region 50. In some examples, bonded region 50 defines a closed region and/or may be described as being a ring or hoop, although bonded region 50 is not limited to being circular and in most instances will not be circular. That is, bonded region 50 is continuous around a perimeter region of moisture capture assembly 100.

The present disclosure generally relates to examples in which moisture capture assembly 100 is positioned at least partially within crotch region 40 that is configured to be positioned adjacent to the wearer's crotch and/or groin area when garment 10 is worn by the wearer. However, such examples are not limiting, and it is to be understood that the various aspects, features, constructions, etc. of garments 10 according to the present disclosure may be applied to any of a variety of articles, including garments 10 that are not configured to be worn adjacent to a wearer's groin area and/or garments that do not include crotch region 40. As examples, aspects of garments 10 according to the present disclosure, such as moisture capture assembly 100 and/or adhesive bonds 60, may be configured to absorb sweat associated with the user's arm pits, may be configured to restrict moisture from penetrating an outer garment to reach the user's skin, etc.

As schematically illustrated in FIGS. 1-3, moisture capture assembly 100 includes an assembly interior side 106 that faces the wearer when garment 10 is worn by the wearer and an assembly exterior side 108 that faces away from the wearer when the garment 10 is worn by the wearer. As additionally schematically illustrated in FIGS. 1-3, moisture capture assembly 100 further includes a moisture retention portion 120 that is configured to absorb and retain moisture from the user, as well as an anti-leak portion 130 that is configured to restrict moisture from exiting moisture retention portion 120. In the present disclosure, moisture retention portion 120 also may be referred to as a moisture retention subassembly 120, and anti-leak portion 130 may be referred to as an anti-leak subassembly 130.

Garment 10 may be configured to absorb and retain any of a variety of fluids, such as may be associated with and/or produced by the wearer while the wearer wears the garment. For example, garment 10 may be configured to absorb and retain blood and/or other menstrual fluids produced by the wearer, and/or to absorb and retain urine produced by the wearer, such as may be associated with an incontinence condition. However, unlike traditional absorbent garments that include absorbent features that are bulky and/or that are assembled within the garment with bulky stitching, the bonded construction of garment 10 as disclosed herein allows for garment 10 to be low-profile and discreet without compromising the leak-proof properties of the garment. Garment 10 may include and/or be any of a variety of garments and/or worn accessories, examples of which include an undergarment, a short (e.g., a pair of shorts), a menstrual pad, an outerwear garment, an activewear garment, leggings, tights, hosiery, a skort, a skirt, etc. In various examples according to the present disclosure, garment 10 is configured to be washed and re-worn numerous times. In this manner, in such examples, garment 10 is distinct from a disposable absorbent garment that is configured to be worn only once, or only a small number of times, before being disposed and replaced.

As schematically illustrated in FIGS. 2-3, the plurality of adhesive bonds 60 includes an internal peripheral bond 56 that is positioned on an interior side of at least a portion of moisture capture assembly 100 and an external peripheral bond 58 positioned on an exterior side of at least a portion of the moisture capture assembly. Specifically, each of internal peripheral bond 56 and external peripheral bond 58 extends at least substantially around a perimeter of moisture capture assembly 100. As described in more detail herein, configuring garment 10 to include each of internal peripheral bond 56 and external peripheral bond 58 may enhance the moisture retention properties of moisture capture assembly 100, and/or may facilitate incorporating the moisture capture assembly into any of a variety of garments without compromising such moisture retention properties.

Additionally, bonding moisture capture assembly 100 to garment base 80 at least partially via internal peripheral bond 56 and external peripheral bond 58 as described herein may enable the moisture capture assembly to be incorporated into a wide range of types of garments 10. For example, several prior art absorbent garments include an absorbent pad that is attached to the garment via material that at least partially defines leg openings of the garment, and/or that otherwise necessarily extends adjacent to the leg openings. By contrast, utilizing adhesive bonds 60 such as internal peripheral bond 56 and/or external peripheral bond 58 as disclosed herein enables moisture capture assembly 100 to be positioned at any desired location within garment 10, such as at a location that is not immediately adjacent to a leg opening. As a result, the constructions disclosed herein are applicable not only to garments 10 in the form of undergarments such as panties, but also to examples of garments such as pants and shorts in which the crotch region is not immediately adjacent to a terminal edge of the garment. Accordingly, the shape and/or form of moisture capture assembly 100 itself is not substantially constrained and/or determined by a shape and/or dimension of garment 10 and/or of garment base 80 in a region occupied by the moisture capture assembly.

As described in more detail herein, various components and/or features of garment 10 may be described with reference to directions defined relative to the garment. For example, and as schematically illustrated in FIGS. 1-3, garment 10 and/or a portion thereof may be described as defining a laterally inward direction 12 and a laterally outward direction 14, such that laterally inward direction 12 generally is directed toward a central region of garment 10 and/or of crotch region 40, and such that laterally outward direction 14 is opposite the laterally inward direction. Additionally, and as schematically illustrated in FIGS. 2-3, garment 10 may be described as defining a transversely inward direction 16 that is directed toward the wearer when garment 10 is worn by the wearer and a transversely outward direction 18 that is opposite the transversely inward direction. In this manner, each of transversely inward direction 16 and transversely outward direction 18 is perpendicular to each of laterally inward direction 12 and laterally outward direction 14. As a more specific example, and as schematically illustrated in FIGS. 2-3, assembly interior side 106 of moisture capture assembly 100 may be described as being spaced apart from assembly exterior side 108 of the moisture capture assembly along transversely inward direction 16. As used herein, a first component may be described as being positioned on an interior side of a second component when the first component is at least partially offset from the second component along transversely inward direction 16. Similarly, as used herein, a first component may be described as being positioned on an exterior side of a second component when the first component is at least partially offset from the second component along transversely outward direction 18.

Although FIGS. 1-3 schematically illustrate garment 10 as being generally flat and/or planar, this is not required of garment 10 due to the nature of the garment's construction from fabric or other flexible materials. Accordingly, it is within the scope of the present disclosure that each of laterally inward direction 12, laterally outward direction 14, transversely inward direction 16, and/or transversely outward direction 18 is not oriented in the same absolute direction at all locations on garment 10. Stated differently, laterally inward direction 12, laterally outward direction 14, transversely inward direction 16, and transversely outward direction 18 may be described as representing directions that are relative to a particular location and/or region of garment 10, irrespective of the configuration and/or orientation of the garment away from such a particular location and/or region.

Each of the plurality of adhesive bonds 60 may operate to bond any of a variety of portions and/or components of garment 10 to one another. In particular, and as schematically illustrated in FIGS. 2-3, the plurality of adhesive bonds 60 may include one or more capture assembly-base bonds 64, each of which operates to bond at least a portion of moisture capture assembly 100 to at least a portion of garment base 80, as described in more detail herein. Additionally or alternatively, and as schematically illustrated in FIGS. 2-3, the plurality of adhesive bonds 60 may include one or more capture assembly internal bonds 66, each of which operates to bond two or more distinct portions and/or components of moisture capture assembly 100 to one another, as described in more detail herein. Additionally or alternatively, and as schematically illustrated in FIGS. 2-3, the plurality of adhesive bonds 60 may include one or more base internal bonds 68, each of which operates to bond two or more distinct portions and/or components of garment base 80 to one another, as described in more detail herein. In some examples, at least one adhesive bond 60 may be described as representing two or more of capture assembly-base bond 64, capture assembly internal bond 66, and/or base internal bond 68. For example, in an example in which a particular adhesive bond 60 operates to bond a portion of moisture capture assembly 100 to each of garment base 80 and to another portion of the moisture capture assembly, such an adhesive bond may be described as being each of a capture assembly-base bond 64 and a capture assembly internal bond 66.

In various examples, the plurality of adhesive bonds 60 may include a plurality of capture assembly-base bonds 64, a plurality of capture assembly internal bonds 66, and/or a plurality of base internal bonds 68. Accordingly, descriptions and/or references herein to a configuration and/or feature of capture assembly-base bond 64, of capture assembly internal bond 66, and/or of base internal bond 68 are to be understood to referring to at least one such adhesive bond 60 of garment 10 without requiring that every such adhesive bond of the garment exhibits such a configuration and/or feature.

Each adhesive bond 60 may be formed in any of a variety of manners. For example, and as schematically illustrated in FIGS. 2-3, each adhesive bond 60 may be formed by an adhesive material 62 that is applied to garment base 80 and/or to moisture capture assembly 100 to assemble garment 10. In such examples, adhesive material 62 may include and/or be any of a variety of materials, examples of which include a tape, an elastic tape, a film, an elastic film, an adhesive, a spray-on adhesive, a liquid curable adhesive, and/or a thermoset adhesive. Additionally or alternatively, one or more adhesive bonds 60 may be formed at least partially via a thermocompression process, such as by applying heat and/or pressure to adhesive material 62 during the manufacture of garment 10.

In some examples, adhesive bond 60 and/or adhesive material 62 is water-resistant, water-repellent, and/or waterproof. Accordingly, in such examples, and as discussed in more detail herein, each such adhesive bond 60 may form a barrier to the passage of moisture and/or bodily fluids, such as to retain such moisture and/or bodily fluids within moisture capture assembly 100 and/or to restrict moisture from entering the moisture capture assembly from an external environment.

In the schematic cross-sectional side views of FIGS. 2-3, each adhesive bond 60 is indicated by an elongate rectangle that overlaps two or more structures and/or layers of garment base 80 and/or of moisture capture assembly 100. In particular, although FIGS. 2-3 schematically illustrate each adhesive bond 60 as having an extent along transversely inward direction 16 and/or along transversely outward direction 18, such an illustration is presented for clarity only, and it is to be understood that each adhesive bond 60 and/or the associated adhesive material 62 may exist primarily, solely, and/or at least substantially between, or at an interface between, the structures that are bonded together via the adhesive bond. Additionally or alternatively, the associated adhesive material may extend into (e.g., having wicked into) the structures that are bonded together via the adhesive bond. Similarly, it is to be understood that the schematic representations of FIGS. 2-3 represent the illustrated components as having a greatly exaggerated extent along the direction parallel to transversely inward direction 16 and transversely outward direction 18 for purposes of clarity.

Figure 10:
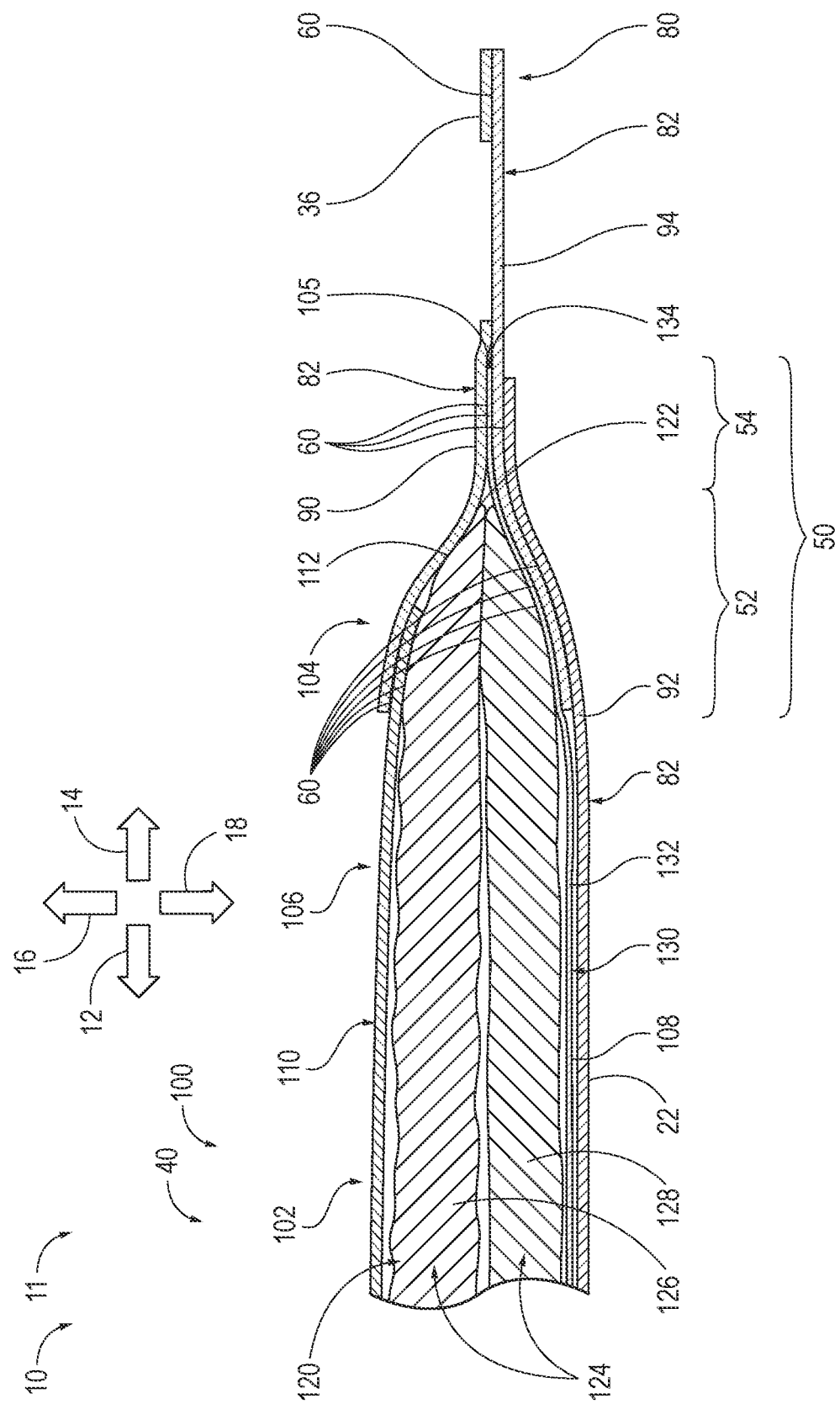
FIG. 10 is a fragmentary cross-sectional top side elevation view of the example garment of FIG. 4.

In the present disclosure, description of locations and/or configurations of various adhesive bonds 60 and/or of various layers of garment 10 often are presented with reference to the cross-sectional views of FIGS. 2-3 and 10. Although the cross-sectional views of FIGS. 2-3 are taken along the line 2-2 of FIG. 1, it is to be understood that such cross-sectional views (including the cross-sectional views of FIG. 10 may correspond to any suitable portion of garment 10 and/or of bonded region 50. In this manner, the cross-sectional views of FIGS. 2-3 and 10 may be understood as being representative of any and/or every location along a perimeter of moisture capture assembly 100. In particular, in some examples, the constructions illustrated in the cross-sectional views of FIGS. 2-3 and 10 extend fully (or at least substantially fully) around a perimeter of moisture capture assembly 100. However, this is not required of all examples of garment 10, and it additionally is within the scope of the present disclosure that the construction of garment 10 may vary at distinct locations along a perimeter of moisture capture assembly 100.

Garment 10 may include any of a variety of features for accommodating and/or engaging the wearer's body. As schematically illustrated in FIGS. 1-3, garment 10 may be described as including a garment interior surface 20 that faces the wearer when the garment is worn by the wearer as well as a garment exterior surface 22 that faces away from the wearer when the garment is worn by the wearer. In particular, in some examples, at least a portion of garment interior surface 20 is configured to directly contact the wearer when garment 10 is worn by the wearer. Stated differently, in some examples, garment 10 is configured such that, when the garment is worn by the wearer, no portion of the garment is positioned directly between garment interior surface 20 and the wearer. Similarly, in some examples, garment 10 is configured such that, when the garment is worn by the wearer, no portion of the garment is positioned distal the wearer relative to garment exterior surface 22.

In some examples, and as schematically illustrated in FIG. 1 and less schematically illustrated in FIGS. 4-5 and 7-8, garment 10 includes a waistband region 30 and/or one or more garment apertures 32. In particular, garment base 80 may at least partially define waistband region 30 and/or each garment aperture 32. In some examples, and as schematically illustrated in FIGS. 1-3 and less schematically illustrated in FIGS. 4-5 and 7-8, each garment aperture 32 defines a leg opening 34 that is configured to receive a leg of the wearer when garment 10 is worn by the wearer. In some such examples, and as schematically illustrated in FIGS. 1-3 and less schematically illustrated in FIGS. 4 and 6-9, garment 10 additionally includes an edge reinforcing strip 36 positioned adjacent to each garment aperture 32. In particular, edge reinforcing strip 36 may be an elastic strip (e.g., a strip of elasticized fabric) configured to conform each leg opening 34 to the wearer's leg. In particular, each edge reinforcing strip 36 may at least partially define the corresponding garment aperture 32 and/or the corresponding leg opening 34. Additionally or alternatively, in some examples, each edge reinforcing strip 36 may be described as lining the corresponding garment aperture 32 and/or the corresponding leg opening 34. In some examples, and as schematically illustrated in FIGS. 2-3, each edge reinforcing strip 36 is bonded to garment base 80 with a corresponding adhesive bond 60.

As schematically illustrated in FIGS. 1-3, moisture capture assembly 100 may be described as including a moisture capture assembly central region 102 and a moisture capture assembly peripheral region 104 that circumferentially encloses the moisture capture assembly central region. Accordingly, and as schematically illustrated in FIGS. 1-3, bonded region 50 may be described as including at least a portion of moisture capture assembly peripheral region 104. Additionally or alternatively, bonded region 50 may be described as extending at least substantially around and/or along a perimeter of moisture capture assembly peripheral region 104.

As additionally schematically illustrated in FIGS. 1-3, garment base 80 may be described as defining a garment lateral edge 28 in a region proximal to moisture capture assembly 100, such that at least a portion of the moisture capture assembly is spaced apart from the garment lateral edge along laterally inward direction 12. That is, garment lateral edge 28 may refer to a terminal edge of garment base 80 at a location that is proximate to, but spatially removed from, moisture capture assembly 100. As an example, garment lateral edge 28 may define garment aperture 32, such as leg opening 34, such that moisture capture assembly 100 is spatially removed from garment aperture 32. That is, in such examples, moisture capture assembly 100 does not extend to garment lateral edge 28.

In some examples, and as schematically illustrated in FIG. 2, bonded region 50 extends from moisture capture assembly peripheral region 104 toward, and/or fully to, garment lateral edge 28. Similarly, in some examples, and as schematically illustrated in FIG. 2, a portion of moisture capture assembly 100 extends fully to garment lateral edge 28. As a more specific example, moisture capture assembly 100 may be described as including and terminating at a moisture capture assembly lateral edge 105, which may define garment lateral edge 28. However, this is not required, and it additionally is within the scope of the present disclosure that bonded region 50 may extend from moisture capture assembly peripheral region 104 to a point that is spaced apart from garment lateral edge 28, such as along laterally inward direction 12. Additionally, it is within the scope of the present disclosure that moisture capture assembly 100 does not extend to garment lateral edge 28, such that moisture capture assembly lateral edge 105 is spaced apart from garment lateral edge 28, such as along laterally inward direction 12.

Bonded region 50 additionally or alternatively may be characterized with reference to a lateral edge of a portion of moisture capture assembly 100. In particular, and as schematically illustrated in FIGS. 1-3, moisture retention portion 120 of moisture capture assembly 100 may be described as including and terminating at a moisture retention portion lateral edge 122. As additionally schematically illustrated in FIGS. 1-3, bonded region 50 may be described as including a laterally inward portion 52 that extends from moisture retention portion lateral edge 122 toward moisture capture assembly central region 102 along laterally inward direction 12 and a laterally outward portion 54 that extends from moisture retention portion lateral edge 122 away from moisture retention portion 120 along laterally outward direction 14. In particular, in some examples, bonded region 50 consists of laterally inward portion 52 and laterally outward portion 54, which are non-overlapping and immediately adjacent to one another. In some examples, and as schematically illustrated in FIGS. 2-3 and less schematically illustrated in FIG. 10, moisture capture assembly lateral edge 105 is spaced apart from moisture retention portion lateral edge 122 along laterally outward direction 14. However, this is not required of all examples of moisture capture assembly 100, and it additionally is within the scope of the present disclosure that moisture retention portion lateral edge 122 is aligned with and/or defines moisture capture assembly lateral edge 105 (as optionally and schematically represented in FIG. 2).

Garment base 80 may have any of a variety of constructions for supporting moisture capture assembly 100 within crotch region 40. In various examples, and as schematically illustrated in FIGS. 1-3 and less schematically illustrated in FIGS. 4-10, garment base 80 includes one or more base layers 82. In particular, in some examples, at least one base layer 82 is bonded to at least a portion of moisture capture assembly 100 via a corresponding capture assembly-base bond 64. Additionally or alternatively, and as schematically illustrated in FIG. 1 and less schematically illustrated in FIGS. 4-9, garment base 80 may include a plurality of base panels 88 that are operatively coupled to one another to collectively form the garment base. In such examples, each base panel 88 may include at least one base layer 82. In such examples, the plurality of base panels 88 may be operatively coupled to one another in any of a variety of manners, such as via stitching and/or via adhesive bonding.

In various examples, and as schematically illustrated in FIGS. 1-3, base layer(s) 82 include an interior base layer 90 that forms at least a portion of garment interior surface 20 and/or an exterior base layer 92 that forms at least a portion of garment exterior surface 22. Base layer(s) 82 further may include an intermediate base layer 94 that is positioned at least partially between one other base layer 82 and moisture capture assembly 100, and/or between two other base layers. In some examples, and as perhaps best schematically illustrated in FIG. 3, intermediate base layer 94 also may define at least a portion of garment interior surface 20 and/or of garment exterior surface 22; however, for the purposes of the present disclosure, such a base layer still is termed an intermediate base layer on account of being positioned between interior base layer 90 and exterior base layer 92. In this manner, intermediate base layer 94 may refer to any base layer 82 that overlies at least a portion of exterior base layer 92 and that underlies at least a portion of interior base layer 90. Each base layer 82 (e.g., interior base layer 90, exterior base layer 92, and/or intermediate base layer 94) may be formed of any of a variety of materials. As examples, each base layer 82 may be at least partially formed of a natural fiber, cotton, a synthetic fiber, polyester, nylon, Spandex™ fabric, and/or combinations thereof.

In the present disclosure, each base layer 82 may be at least partially characterized with reference to one or more lateral edges thereof. For example, and as schematically illustrated in FIGS. 2-3, each base layer 82 may be described as including and terminating at a respective base layer lateral inward edge 84, such that the base layer extends away from the respective base layer lateral inward edge along laterally outward direction 14. Additionally or alternatively, and as schematically illustrated in FIGS. 2-3, each base layer 82 may be described as including and terminating at a respective base layer lateral outward edge 86, such that the base layer extends away from the respective base layer lateral outward edge along laterally inward direction 12.

As used herein, directional terms such as "overlie," "above," "underlie," "below," and the like generally refer to relative positions as viewed from the side of garment 10 with garment interior surface 20 facing upwards, as in the schematic views of FIGS. 2-3. In particular, a first component may be described as overlying a second component, and/or as being positioned above the second component, when the first component is spatially offset from the second component along transversely inward direction 16. Similarly, a first component may be described as underlying a second component, and/or as being positioned under the second component, when the first component is spatially offset from the second component along transversely outward direction 18.

Moisture capture assembly 100 and/or moisture retention portion 120 may have any of a variety of constructions for absorbing and capturing moisture from the wearer. In some examples, and as schematically illustrated in FIGS. 2-3 and less schematically illustrated in FIG. 10, moisture retention portion 120 includes one or more moisture retention layers 124, such as a first moisture retention layer 126 and a second moisture retention layer 128. In some such examples, and as schematically illustrated in FIGS. 2-3 and less schematically illustrated in FIG. 10, each of first moisture retention layer 126 and second moisture retention layer 128 extends to (and thus at least partially defines) moisture retention portion lateral edge 122. When present, first moisture retention layer 126 and second moisture retention layer 128 may be formed of the same and/or similar materials, or may be at least partially formed of different materials.

In some examples, first moisture retention layer 126 and second moisture retention layer 128 are operatively coupled to one another. In particular, and as schematically illustrated in FIGS. 2-3, first moisture retention layer 126 and second moisture retention layer 128 may be bonded to one another via at least one capture assembly internal bond 66. In such examples, and as schematically illustrated in FIGS. 2-3 and less schematically illustrated in FIG. 10, capture assembly internal bond 66 that bonds first moisture retention layer 126 and second moisture retention layer 128 to one another may be positioned only (e.g., fully and/or exclusively) or at least substantially in laterally inward portion 52 of bonded region 50. However, this is not required of all examples of moisture capture assembly 100, and it also is within the scope of the present disclosure that capture assembly internal bond 66 that bonds first moisture retention layer 126 and second moisture retention layer 128 may be positioned within each of laterally inward portion 52 and laterally outward portion 54 of bonded region 50.

In some examples, and as schematically illustrated in FIGS. 1-3 and less schematically illustrated in FIGS. 7-10, moisture retention portion 120 of moisture capture assembly 100 includes a wicking layer 110 that is configured to wick moisture away from the wearer. In particular, in such examples, wicking layer 110 may be configured to draw moisture away from the wearer, such as via capillary action, and to direct and/or convey the moisture to moisture retention layer(s) 124. In such examples, wicking layer 110 may be positioned and/or bonded within moisture capture assembly 100 in any of a variety of manners. For example, and as schematically illustrated in FIGS. 1-3 and less schematically illustrated in FIGS. 7-10, wicking layer 110 may extend within each of moisture capture assembly central region 102 and moisture capture assembly peripheral region 104. In some examples, wicking layer 110 is operatively coupled to moisture retention portion 120, such as to first moisture retention layer 126. In particular, in some examples, and as schematically illustrated in FIGS. 2-3, wicking layer 110 and moisture retention portion 120 are bonded to one another via at least one adhesive bond 60, such as via at least one capture assembly internal bond 66. In some examples, and as schematically illustrated in FIGS. 2-3 and less schematically illustrated in FIG. 10, wicking layer 110 at least partially defines assembly interior side 106 of moisture capture assembly 100.

With particular reference to the cross-sectional views of FIGS. 2-3 and 10, a configuration of wicking layer 110 also may be characterized with reference to a wicking layer lateral edge 112 thereof, which represents a terminal edge of the wicking layer. For example, and as schematically illustrated in FIGS. 2-3 and less schematically illustrated in FIG. 10, wicking layer lateral edge 112 may be aligned with moisture retention portion lateral edge 122. However, this is not required of all examples of moisture capture assembly 100, and it additionally is within the scope of the present disclosure that wicking layer lateral edge 112 may be spaced apart from moisture retention portion lateral edge 122 along laterally inward direction 12 or along laterally outward direction 14. In particular, in an example in which wicking layer lateral edge 112 is spaced apart from moisture retention portion lateral edge 122 along laterally outward direction 14, wicking layer 110 may extend within each of laterally inward portion 52 and laterally outward portion 54 of bonded region 50. In some examples, such as when wicking layer lateral edge 112 is aligned with moisture retention portion lateral edge 122 or is spaced apart from the moisture retention portion lateral edge along laterally outward direction 14, the wicking layer lateral edge may define moisture capture assembly lateral edge 105 (as optionally and schematically represented in FIG. 2). Alternatively, in some examples, such as when wicking layer lateral edge 112 is spaced apart from moisture retention portion lateral edge 122 along laterally inward direction 12, the wicking layer lateral edge also may be spaced apart from moisture capture assembly lateral edge 105 along the laterally inward direction.

As used herein, the term "aligned," as used to describe a relative position of a first edge relative to a second edge, generally refers to a configuration in which the first edge and the second edge are positioned at respective locations that are not spatially separated from one another along laterally inward direction 12 or along laterally outward direction 14, but which may be spatially separated from one another along transversely inward direction 16 or along transversely outward direction 18. However, it is to be understood that a description herein of two or more components as being "aligned" does not necessarily mean that the two or more components are exactly and/or precisely aligned with one another. For example, as known in the art, garment construction is not perfect, and the imprecision introduced by human- and/or machine-performed manufacturing can introduce slight misalignments between components that nominally are intended or designed to be aligned with one another. Accordingly, for the purposes of the present disclosure, the term "aligned" is intended to encompass configurations in which the components are perfectly aligned, as well as configurations in which the components are slightly misaligned as a result of manufacturing tolerances.

Anti-leak portion 130 of moisture capture assembly 100 may include any of a variety of components and/or features for restricting moisture from exiting the moisture capture assembly. For example, and as schematically illustrated in FIGS. 2-3 and less schematically illustrated in FIG. 10, anti-leak portion 130 may include and/or be a moisture barrier layer 132 that is operatively coupled to moisture retention portion 120. In particular, in some examples, and as schematically illustrated in FIGS. 2-3, moisture barrier layer 132 is bonded to moisture retention portion 120 via at least one adhesive bond 60, such as via at least one capture assembly internal bond 66. When present, moisture barrier layer 132 may include and/or be any of a variety of materials, such as a moisture-impermeable film. Additionally or alternatively, in some examples, and as schematically illustrated in FIG. 2, anti-leak portion 130 may include and/or be a moisture barrier treatment 136 and/or a moisture barrier film that is applied to moisture retention portion 120, such as to moisture retention layer 124 (e.g., to second moisture retention layer 128). In some examples, and as schematically illustrated in FIGS. 2-3 and less schematically illustrated in FIG. 10, moisture barrier layer 132 at least partially defines assembly exterior side 108 of moisture capture assembly 100.

Each portion of moisture capture assembly 100 may be formed of any of a variety of materials. As examples, each of moisture capture assembly 100, moisture retention portion 120, first moisture retention layer 126, second moisture retention layer 128, wicking layer 110, and/or moisture barrier layer 132 may be at least partially formed of a natural fiber, cotton, a synthetic fiber, polyester, nylon, Spandex™ fabric, and/or combinations thereof.

With particular reference to the cross-sectional views of FIGS. 2-3 and 10, a configuration of moisture barrier layer 132 also may be characterized with reference to a moisture barrier layer lateral edge 134 thereof, which represents a terminal edge of the moisture barrier layer. For example, and as schematically illustrated in FIGS. 2-3 and less schematically illustrated in FIG. 10, moisture barrier layer lateral edge 134 may be spaced apart from moisture retention portion lateral edge 122 along laterally outward direction 14. In particular, in such examples, moisture barrier layer 132 may extend within each of laterally inward portion 52 and laterally outward portion 54 of bonded region 50. However, this is not required of all examples of moisture capture assembly 100, and it additionally is within the scope of the present disclosure that moisture barrier layer lateral edge 134 may be aligned with moisture retention portion lateral edge 122 (as optionally and schematically represented in FIG. 2), or may be spaced apart from the moisture retention portion lateral edge along the laterally inward direction 12. In some examples, such as when moisture barrier layer lateral edge 134 is aligned with moisture retention portion lateral edge 122 or is spaced apart from the moisture retention portion lateral edge along laterally outward direction 14, the moisture barrier layer lateral edge may define moisture capture assembly lateral edge 105. Alternatively, in some examples, such as when moisture barrier layer lateral edge 134 is spaced apart from moisture retention portion lateral edge 122 along laterally inward direction 12, the moisture barrier layer lateral edge also may be spaced apart from moisture capture assembly lateral edge 105 along laterally inward direction 12.

Each capture assembly-base bond 64 may have any of a variety of configurations and/or locations within garment 10 so as to bond at least a portion of moisture capture assembly 100 to at least a portion of garment base 80. In some examples, and as schematically illustrated in FIGS. 2-3, capture assembly-base bond 64 (e.g., at least one capture assembly-base bond) is positioned only in laterally inward portion 52 of bonded region 50. Additionally or alternatively, in some examples, and as schematically illustrated in FIGS. 2-3, capture assembly-base bond 64 (e.g., at least one capture assembly-base bond) is positioned in laterally outward portion 54 of bonded region 50. Additionally or alternatively, in some examples, and as schematically illustrated in FIGS. 2-3, capture assembly-base bond 64 (e.g., at least one capture assembly-base bond) extends within each of laterally inward portion 52 and laterally outward portion 54 of bonded region 50.

Additionally, each capture assembly-base bond 64 may operate to bond any of a variety of portions of moisture capture assembly 100 to any of a variety of portions of garment base 80. In particular, in some examples, and as schematically illustrated in FIGS. 2-3, capture assembly-base bond 64 (e.g., at least one capture assembly-base bond) directly bonds at least one base layer 82 to assembly interior side 106 of moisture capture assembly 100. For example, capture assembly-base bond 64 may operate to bond a base layer (e.g., interior base layer 90) directly to assembly interior side 106 of the moisture capture assembly 100 (e.g., to wicking layer 110 and/or to first moisture retention layer 126).

Additionally or alternatively, in some examples, and as schematically illustrated in FIGS. 2-3, capture assembly-base bond 64 (e.g., at least one capture assembly-base bond) directly bonds at least one base layer 82 to assembly exterior side 108 of moisture capture assembly 100. For example, capture assembly-base bond 64 may operate to bond a base layer 82 (e.g., intermediate base layer 94 and/or exterior base layer 92) directly to assembly exterior side 108 of the moisture capture assembly (e.g., to second moisture retention layer 128 and/or to moisture barrier layer 132).

In some examples, and as schematically illustrated in FIGS. 2-3, at least one capture assembly-base bond 64 and/or at least one base internal bond 68 may include and/or be internal peripheral bond 56 or external peripheral bond 58. Stated differently, and as schematically illustrated in FIGS. 2-3, each of internal peripheral bond 56 and/or external peripheral bond 58 may be an example and/or an instance of capture assembly-base bond 64 and/or of base internal bond 68.

Examples of manners in which internal peripheral bond 56, external peripheral bond 58, and anti-leak portion 130 of moisture capture assembly 100 collectively resist leakage of moisture also may be understood with reference to FIGS. 2-3. As discussed, each adhesive bond 60 may be formed by an adhesive material 62 that is water-resistant, water-repellent, and/or waterproof. Accordingly, each of internal peripheral bond 56 and external peripheral bond 58 may be described as representing a barrier against the leakage of moisture across the bond. Similarly, moisture barrier layer 132 of anti-leak portion 130 also may be described as representing a barrier against the leakage of moisture across the moisture barrier layer. Accordingly, and with reference to the schematic cross-sectional views of FIGS. 2-3, moisture that is incident upon moisture capture assembly 100 via assembly interior side 106 is restricted from escaping moisture retention portion 120 other than via the assembly internal side, since each other path out of the moisture retention portion is blocked by internal peripheral bond 56 and/or by moisture barrier layer 132. In this manner, anti-leak portion 130 and the plurality of adhesive bonds 60 may prevent leakage of moisture out of moisture retention portion 120 via a portion of garment base 80 underlying the moisture retention portion (e.g., via exterior base layer 92) as well as via a peripheral edge of moisture capture assembly 100. Additionally, in this manner, garment 10 also is protected against ingress of moisture from exterior the garment, since each path to moisture retention portion 120 from exterior the garment is blocked by exterior peripheral bond 58 and/or by moisture barrier layer 132. Thus, garment 10 also may protect the wearer from discomfort resulting from a wetting of moisture capture assembly 100 from moisture that did not originate from the wearer, such as water in a swimming pool occupied by the wearer, water on a seating surface upon which the wearer is seated, etc.

When present, interior base layer 90 may have any suitable position, orientation, and/or extent relative to moisture capture assembly 100, moisture retention portion 120, and/or bonded region 50. In some examples, and as schematically illustrated in FIGS. 2-3 and less schematically illustrated in FIG. 10, interior base layer 90 and moisture retention portion 120 are directly bonded to one another via a corresponding capture assembly-base bond 64 (labeled in FIGS. 2-3). In particular, in some examples, interior base layer 90 is directly bonded to wicking layer 110 and/or to moisture barrier layer 132 via respective capture assembly-base bonds 64 (labelled in FIGS. 2-3).

In some examples, and as schematically illustrated in FIGS. 2-3 and less schematically illustrated in FIG. 10, at least a portion of interior base layer 90 overlies at least a portion of moisture capture assembly 100, such as at least a portion of moisture capture assembly peripheral region 104. Stated differently, in some examples, interior base layer 90 overlies at least a portion of moisture capture assembly 100 within moisture capture assembly peripheral region 104 and/or within laterally inward portion 52 of bonded region 50. Additionally or alternatively, in some examples, and as schematically illustrated in FIGS. 2-3 and less schematically illustrated in FIG. 10, interior base layer 90 extends within each of laterally inward portion 52 and laterally outward portion 54 of bonded region 50. While FIGS. 2-3 schematically illustrate interior base layer 90 as overlying moisture capture assembly 100 as a single flat layer, this is not required of all examples of garment 10. As examples, it also is within the scope of the present disclosure that interior base layer 90 may be folded, doubled over, and/or otherwise characterized by two or more adjacent layers within a portion of moisture capture assembly peripheral region 104 within which interior base layer 90 overlies moisture capture assembly 100.

In some examples, and as schematically illustrated in FIGS. 2-3 and less schematically illustrated in FIG. 10, base layer lateral inward edge 84 of interior base layer 90 is spaced apart from moisture retention portion lateral edge 122 along laterally inward direction 12. Additionally or alternatively, in some examples, and as schematically illustrated in FIG. 2, base layer lateral outward edge 86 of interior base layer 90 is aligned with moisture capture assembly lateral edge 105 and/or with moisture retention portion lateral edge 122. In other examples, and as schematically illustrated in FIGS. 2-3, base layer lateral outward edge 86 of interior base layer 90 is spaced apart from moisture capture assembly lateral edge 105 and/or from moisture retention portion lateral edge 122 along laterally inward direction 12 (as illustrated in FIG. 2) or along laterally outward direction 14 (as illustrated in FIGS. 2-3).

In some examples, a configuration of interior base layer 90 additionally or alternatively may be characterized with reference to wicking layer 110. For example, and as schematically illustrated in FIGS. 2-3 and less schematically illustrated in FIG. 10, base layer lateral inward edge 84 of interior base layer 90 may be spaced apart from wicking layer lateral edge 112 along laterally inward direction 12. Additionally or alternatively, in some examples, interior base layer 90 may overlie at least a portion of wicking layer 110 within moisture capture assembly peripheral region 104 and/or within laterally inward portion 52 of bonded region 50. Additionally or alternatively, in some examples, base layer lateral outward edge 86 of interior base layer 90 may be aligned with wicking layer lateral edge 112. In other examples, and as schematically illustrated in FIGS. 2-3, base layer lateral outward edge 86 of interior base layer 90 may be spaced apart from wicking layer lateral edge 112 along laterally outward direction 14.

In some examples, a configuration of interior base layer 90 additionally or alternatively may be characterized with reference to moisture barrier layer 132. For example, and as schematically illustrated in FIGS. 2-3 and less schematically illustrated in FIG. 10, base layer lateral inward edge 84 of interior base layer 90 may be spaced apart from moisture barrier layer lateral edge 134 along laterally inward direction 12. Additionally or alternatively, in some examples, interior base layer 90 may overlie at least a portion of moisture barrier layer 132 within moisture capture assembly peripheral region 104, within laterally inward portion 52 of bonded region 50, and/or within laterally outward portion 54 of the bonded region. Additionally or alternatively, in some examples, base layer lateral outward edge 86 of interior base layer 90 may be aligned with moisture barrier layer lateral edge 134. In other examples, and as schematically illustrated in FIGS. 2-3, base layer lateral outward edge 86 of interior base layer 90 may be spaced apart from moisture barrier layer lateral edge 134 along laterally inward direction 12 (as illustrated in FIG. 2) or along laterally outward direction 14 (as illustrated in FIGS. 2-3).

In some examples, interior base layer 90 defines a closed region and/or may be described as being a closed structure. That is, interior base layer 90 is continuous around a perimeter region of moisture capture assembly 100, such as generally coinciding with bonded region 50.

When present, exterior base layer 92 may have any suitable position, orientation, and/or extent relative to moisture capture assembly 100, moisture retention portion 120, and/or bonded region 50. In some examples, exterior base layer 92 and moisture retention portion 120 are directly bonded to one another via a corresponding capture assembly-base bond 64. In particular, in some examples, exterior base layer 92 is directly bonded to wicking layer 110 and/or to moisture barrier layer 132 via respective capture assembly-base bonds 64.

In some examples, and as schematically illustrated in FIGS. 2-3 and less schematically illustrated in FIG. 10, at least a portion of exterior base layer 92 underlies at least a portion of moisture capture assembly 100, such as at least a portion of moisture capture assembly peripheral region 104. Stated differently, in some examples, exterior base layer 92 underlies at least a portion of moisture capture assembly 100 within moisture capture assembly peripheral region 104 and/or within laterally inward portion 52 of bonded region 50. Additionally or alternatively, in some examples, and as schematically illustrated in FIGS. 2-3 and less schematically illustrated in FIG. 10, exterior base layer 92 extends within each of laterally inward portion 52 and laterally outward portion 54 of bonded region 50. While FIGS. 2-3 schematically illustrate exterior base layer 92 as underlying moisture capture assembly 100 as a single flat layer, this is not required of all examples of garment 10. As examples, it also is within the scope of the present disclosure that exterior base layer 92 may be folded, doubled over, and/or otherwise characterized by two or more adjacent layers within a portion of moisture capture assembly peripheral region 104 within which interior base layer 90 underlies moisture capture assembly 100.

In some examples, and as schematically illustrated in FIG. 2, base layer lateral inward edge 84 of exterior base layer 92 is spaced apart from moisture retention portion lateral edge 122 along laterally inward direction 12. Additionally or alternatively, in some examples, and as schematically illustrated in FIG. 2, base layer lateral outward edge 86 of exterior base layer 92 is aligned with moisture capture assembly lateral edge 105 and/or with moisture retention portion lateral edge 122. In other examples, and as schematically illustrated in FIGS. 2-3, base layer lateral outward edge 86 of exterior base layer 92 is spaced apart from moisture capture assembly lateral edge 105 and/or from moisture retention portion lateral edge 122 along laterally inward direction 12 (as illustrated in FIG. 2) or along laterally outward direction 14 (as illustrated in FIGS. 2-3).

In some examples, a configuration of exterior base layer 92 additionally or alternatively may be characterized with reference to wicking layer 110. For example, and as schematically illustrated in FIG. 2, base layer lateral inward edge 84 of exterior base layer 92 may be spaced apart from wicking layer lateral edge 112 along laterally inward direction 12. Additionally or alternatively, in some examples, exterior base layer 92 may underlie at least a portion of wicking layer 110 within moisture capture assembly peripheral region 104 and/or within laterally inward portion 52 of bonded region 50. Additionally or alternatively, in some examples, base layer lateral outward edge 86 of exterior base layer 92 may be aligned with wicking layer lateral edge 112. In other examples, and as schematically illustrated in FIGS. 2-3, base layer lateral outward edge 86 of exterior base layer 92 may be spaced apart from wicking layer lateral edge 112 along laterally inward direction 12 or along laterally outward direction 14.

In some examples, a configuration of exterior base layer 92 additionally or alternatively may be characterized with reference to moisture barrier layer 132. For example, and as schematically illustrated in FIG. 2, base layer lateral inward edge 84 of exterior base layer 92 may be spaced apart from moisture barrier layer lateral edge 134 along laterally inward direction 12. Additionally or alternatively, in some examples, exterior base layer 92 may underlie at least a portion of moisture barrier layer 132 within moisture capture assembly peripheral region 104, within laterally inward portion 52 of bonded region 50, and/or within laterally outward portion 54 of the bonded region. Additionally or alternatively, in some examples, base layer lateral outward edge 86 of exterior base layer 92 may be aligned with moisture barrier layer lateral edge 134. In other examples, and as schematically illustrated in FIGS. 2-3, base layer lateral outward edge 86 of exterior base layer 92 may be spaced apart from moisture barrier layer lateral edge 134 along laterally inward direction 12 (as illustrated in FIG. 2) or along laterally outward direction 14 (as illustrated in FIGS. 2-3).

In some examples, as illustrated in FIG. 3, exterior base layer 92 may coincide with, or generally may be coextensive with, moisture capture assembly 100.

When present, intermediate base layer 94 may have any suitable position, orientation, and/or extent relative to moisture capture assembly 100, moisture retention portion 120, and/or bonded region 50. In some examples, intermediate base layer 94 and moisture retention portion 120 are directly bonded to one another via a corresponding capture assembly-base bond 64. In particular, in some examples, intermediate base layer 94 is directly bonded to wicking layer 110 and/or to moisture barrier layer 132 (as schematically illustrated in FIGS. 2-3) via respective capture assembly-base bonds 64.

In some examples, and as schematically illustrated in FIGS. 2-3 and less schematically illustrated in FIG. 10, at least a portion of intermediate base layer 94 underlies at least a portion of moisture capture assembly 100, such as at least a portion of moisture capture assembly peripheral region 104. Stated differently, in some examples, intermediate base layer 94 underlies at least a portion of moisture capture assembly 100 within moisture capture assembly peripheral region 104 and/or within laterally inward portion 52 of bonded region 50. Additionally or alternatively, in some examples, and as schematically illustrated in FIGS. 2-3 and less schematically illustrated in FIG. 10, intermediate base layer 94 extends within each of laterally inward portion 52 and laterally outward portion 54 of bonded region 50.

In some examples, and as schematically illustrated in FIGS. 2-3 and less schematically illustrated in FIG. 10, base layer lateral inward edge 84 of intermediate base layer 94 is spaced apart from moisture retention portion lateral edge 122 along laterally inward direction 12. Additionally or alternatively, in some examples, and as schematically illustrated in FIG. 2, base layer lateral outward edge 86 of intermediate base layer 94 is aligned with moisture capture assembly lateral edge 105 and/or with moisture retention portion lateral edge 122. In other examples, and as schematically illustrated in FIGS. 2-3, base layer lateral outward edge 86 of intermediate base layer 94 is spaced apart from moisture capture assembly lateral edge 105 and/or from moisture retention portion lateral edge 122 along laterally inward direction 12 (as illustrated in FIG. 2) or along laterally outward direction 14 (as illustrated in FIGS. 2-3).

In some examples, a configuration of intermediate base layer 94 additionally or alternatively may be characterized with reference to wicking layer 110. For example, and as schematically illustrated in FIGS. 2-3 and less schematically illustrated in FIG. 10, base layer lateral inward edge 84 of intermediate base layer 94 may be spaced apart from wicking layer lateral edge 112 along laterally inward direction 12. Additionally or alternatively, in some examples, intermediate base layer 94 may underlie at least a portion of wicking layer 110 within moisture capture assembly peripheral region 104 and/or within laterally inward portion 52 of bonded region 50. Additionally or alternatively, in some examples, base layer lateral outward edge 86 of intermediate base layer 94 may be aligned with wicking layer lateral edge 112. In other examples, and as schematically illustrated in FIGS. 2-3, base layer lateral outward edge 86 of intermediate base layer 94 may be spaced apart from wicking layer lateral edge 112 along laterally inward direction 12 or along laterally outward direction 14.

In some examples, a configuration of intermediate base layer 94 additionally or alternatively may be characterized with reference to moisture barrier layer 132. For example, and as schematically illustrated in FIGS. 2-3 and less schematically illustrated in FIG. 10, base layer lateral inward edge 84 of intermediate base layer 94 may be spaced apart from moisture barrier layer lateral edge 134 along laterally inward direction 12. Additionally or alternatively, in some examples, intermediate base layer 94 may underlie at least a portion of moisture barrier layer 132 within moisture capture assembly peripheral region 104, within laterally inward portion 52 of bonded region 50, and/or within laterally outward portion 54 of the bonded region. Additionally or alternatively, in some examples, base layer lateral outward edge 86 of intermediate base layer 94 may be aligned with moisture barrier layer lateral edge 134. In other examples, and as schematically illustrated in FIGS. 2-3, base layer lateral outward edge 86 of intermediate base layer 94 may be spaced apart from moisture barrier layer lateral edge 134 along laterally inward direction 12 (as illustrated in FIG. 2) or along laterally outward direction 14 (as illustrated in FIGS. 2-3).

In examples in which garment 10 includes a plurality of base layers 82 that are bonded to one another, the base layers may be bonded to one another in any of a variety of manners. In particular, in various examples, and as schematically illustrated in FIGS. 2-3, two or more of interior base layer 90, exterior base layer 92, and/or intermediate base layer 94 are bonded to one another via corresponding base internal bonds 68. In some examples, at least one base internal bond 68 is positioned only in laterally inward portion 52 of bonded region. Additionally or alternatively, at least one base internal bond 68 may be positioned only in laterally outward portion 54 of bonded region 50. Additionally or alternatively, at least one base internal bond 68 may extend within each of laterally inward portion 52 and laterally outward portion 54 of bonded region 50. In particular, FIG. 3 schematically illustrates an example in which base internal bond 68 that bonds exterior base layer 92 and intermediate base layer 94 to one another extends within each of laterally inward portion 52 and laterally outward portion 54.

In examples in which the plurality of base layers 82 includes interior base layer 90 and intermediate base layer 94, the interior base layer and the intermediate base layer may have any suitable relative orientation. As examples, base layer lateral inward edge 84 of interior base layer 90 may be aligned with base layer lateral inward edge 84 of intermediate base layer 94, or may be spaced apart from the base layer lateral inward edge of the intermediate base layer. More specifically, the base layer lateral inward edge of the interior base layer may be spaced apart from the base layer lateral inward edge of the intermediate base layer along laterally inward direction 12 or along laterally outward direction 14. As additional examples, base layer lateral outward edge 86 of interior base layer 90 may be aligned with base layer lateral outward edge 86 of intermediate base layer 94, or may be spaced apart from the base layer lateral outward edge of the intermediate base layer. More specifically, the base layer lateral outward edge of the interior base layer may be spaced apart from the base layer lateral outward edge of the intermediate base layer along laterally inward direction 12 or along laterally outward direction 14. In particular, in the example of FIGS. 3 and 10, the base layer lateral outward edge of the interior base layer is spaced apart from the base layer lateral outward edge of the intermediate base layer along the laterally inward direction. In some examples, such as in the example of FIGS. 3 and 10, interior base layer 90 and intermediate base layer 94 are directly bonded to one another via a corresponding base internal bond 68 (labeled in FIG. 3).

In examples in which the plurality of base layers 82 includes interior base layer 90 and exterior base layer 92, the interior base layer and the exterior base layer may have any suitable relative orientation. As examples, base layer lateral outward edge 86 of interior base layer 90 may be aligned with base layer lateral outward edge 86 of exterior base layer 92, or may be spaced apart from the base layer lateral outward edge of the exterior base layer. More specifically, the base layer lateral outward edge of the interior base layer may be spaced apart from the base layer lateral outward edge of the exterior base layer along laterally inward direction 12 or along laterally outward direction 14. In particular, FIGS. 3 and 10 illustrate an example in which the base layer lateral outward edge of the interior base layer is approximately aligned with the base layer lateral outward edge of the exterior base layer, but is slightly spaced apart from the base layer lateral outward edge of the exterior base layer along the laterally outward direction. In some examples, interior base layer 90 and exterior base layer 92 are directly bonded to one another via a corresponding base internal bond 68. In the example of FIGS. 3 and 10, however, interior base layer 90 and exterior base layer 92 are operatively coupled to one another only via intermediate base layer 94.

In examples in which the plurality of base layers 82 includes exterior base layer 92 and intermediate base layer 94, the exterior base layer and the intermediate base layer may have any suitable relative orientation. As examples, base layer lateral outward edge 86 of exterior base layer 92 may be aligned with base layer lateral outward edge 86 of intermediate base layer 94, or may be spaced apart from the base layer lateral outward edge of the intermediate base layer. More specifically, the base layer lateral outward edge of the exterior base layer may be spaced apart from the base layer lateral outward edge of the intermediate base layer along laterally inward direction 12 or along laterally outward direction 14. In particular, in the example of FIGS. 3 and 10, the base layer lateral outward edge of the exterior base layer is spaced apart from the base layer lateral outward edge of the intermediate base layer along the laterally inward direction. In some examples, such as in the example of FIGS. 3 and 10, exterior base layer 92 and intermediate base layer 94 are directly bonded to one another via a corresponding base internal bond 68 (labeled in FIG. 3).

Turning more specifically to example garment 11 illustrated in FIGS. 4-10, example garment 11 represents an example of garment 10 in the form of a short (e.g., a pair shorts), such as may be worn as an undergarment and/or as nightwear. In particular, FIGS. 4-9 illustrate various aspects of the outer surfaces of example garment 11. FIG. 10 is a cross-sectional view illustrating the configuration of base layers 82 and of the components of moisture capture assembly 100 within bonded region 50 and/or within moisture capture assembly peripheral region 104, while FIG. 3 is a schematic representation of the configuration illustrated in FIG. 10. As discussed, it is to be understood that the configuration illustrated in FIGS. 3 and 10 may be exhibited at any of a variety of locations along moisture capture assembly peripheral region 104. For example, the configuration illustrated in FIGS. 3 and 10 may be representative of every location along moisture capture assembly peripheral region 104, or may be representative of only a portion of the moisture capture assembly peripheral region.

As illustrated in FIGS. 4-9, garment base 80 of example garment 11 includes a plurality of base panels 88 that are assembled together partially via adhesive bonds 60 (not labeled in FIGS. 4-9) and partially via stitching. In portions of garment base 80 extending between bonded region 50 and each garment aperture 32, the sole base layer 82 of the garment base is intermediate base layer 94. In particular, although intermediate base layer 94 defines each of garment interior surface 20 and garment exterior surface 22 in such regions, this base layer 82 still represents an example of intermediate base layer 94 because this base layer is positioned between interior base layer 90 and exterior base layer 92 within bonded region 50. As illustrated in FIGS. 4 and 6-10, example garment 11 additionally includes edge reinforcing strip 36 positioned adjacent to each garment aperture 32, such that each edge reinforcing strip at least partially defines the corresponding garment aperture and the corresponding leg opening 34. In example garment 11, and as schematically illustrated in FIG. 3, each edge reinforcing strip 36 is bonded to garment base 80 (specifically, to intermediate base layer 94) via a corresponding adhesive bond 60.

Turning more specifically to the cross-sectional views of FIGS. 3 and 10, moisture retention portion 120 of example garment 11 includes wicking layer 110, first moisture retention layer 126, and second moisture retention layer 128 bonded to one another via corresponding capture assembly internal bonds 66. Specifically, in this example, wicking layer 110 is bonded to first moisture retention layer 126 via a corresponding capture assembly internal bond 66 that extends from a location that is spaced apart from base layer lateral inward edge 84 of interior base layer 90 along laterally inward direction 12 to wicking layer lateral edge 112. In this example, wicking layer lateral edge 112 is aligned with moisture retention portion lateral edge 122. Additionally, in this example, first moisture retention layer 126 is bonded to second moisture retention layer 128 via a corresponding capture assembly internal bond 66 that extends to moisture retention portion lateral edge 122.

As illustrated in FIGS. 3 and 10, anti-leak portion of example garment 11 includes moisture barrier layer 132 in the form of a moisture-impermeable film that is bonded to moisture retention portion 120. Specifically, in this example, moisture barrier layer 132 is bonded to second moisture retention layer 128 via a corresponding capture assembly internal bond 66 that extends to moisture retention portion lateral edge 122. In this example, moisture barrier layer 132 itself extends beyond moisture retention portion lateral edge 122, such that moisture barrier layer lateral edge 134 is spaced apart from moisture retention portion lateral edge 122 along laterally outward direction 14. Thus, in this example, moisture barrier layer 132 represents the portion of moisture capture assembly 100 with the greatest extent in laterally outward direction 14, such that moisture barrier layer lateral edge 134 represents moisture capture assembly lateral edge 105.

As illustrated in FIGS. 3 and 10, garment base 80 of example garment 11 includes interior base layer 90, exterior base layer 92, and intermediate base layer 94. In particular, in this example, interior base layer 90 is bonded to wicking layer 110 via internal peripheral bond 56, which takes the form of a corresponding capture assembly-base bond 64, such that base layer lateral inward edge 84 of interior base layer 90 is spaced apart from wicking layer lateral edge 112 along laterally inward direction 12. In this manner, in this example, interior base layer 90 overlies moisture retention portion 120 within moisture capture assembly peripheral region 104. In this example, interior base layer 90 further extends along laterally outward direction 14 such that base layer lateral outward edge 86 of interior base layer 90 is spaced apart from moisture retention portion lateral edge 122 along the laterally outward direction. In particular, in laterally outward portion 54 of bonded region 50, interior base layer 90 is directly bonded to moisture barrier layer 132 via a corresponding capture assembly-base bond 64. This corresponding capture assembly-base bond further extends beyond moisture barrier layer lateral edge 134 to additionally bond interior base layer 90 directly to intermediate base layer 94. Accordingly, this adhesive bond 60 also may be referred to as base internal bond 68, at least in the region in which interior base layer 90 is directly bonded to intermediate base layer 94. In this manner, in this example, base layer lateral outward edge 86 of interior base layer 90 also is spaced apart from the moisture barrier layer lateral edge along laterally outward direction 14.

In the example of FIGS. 3 and 10, intermediate base layer 94 is bonded directly to interior base layer 90 as discussed above, and further is bonded directly to moisture barrier layer 132 via a corresponding capture assembly-base bond 64. In this example, intermediate base layer 94 extends along laterally outward direction 14 such that base layer lateral outward edge 86 of the intermediate base layer is spaced apart from the base layer lateral outward edge of interior base layer 90. Additionally, in this example, base layer lateral inward edge 84 of intermediate base layer 94 is positioned within, or proximate to, moisture capture assembly peripheral region 104. By contrast, in this example, exterior base layer 92 spans a full width of moisture capture assembly 100 and underlies the moisture capture assembly within moisture capture assembly central region 102 and moisture capture assembly peripheral region 104. In this example, exterior base layer 92 is bonded directly to intermediate base layer 94 via external peripheral bond 58, which takes the form of a corresponding base internal bond 68. In this example, base layer lateral outward edge 86 of exterior base layer 92 is generally aligned with base layer lateral outward edge 86 of interior base layer 90, but is slightly spaced apart from the base layer lateral outward edge of the interior base layer along laterally inward direction 12.

Figure 11:
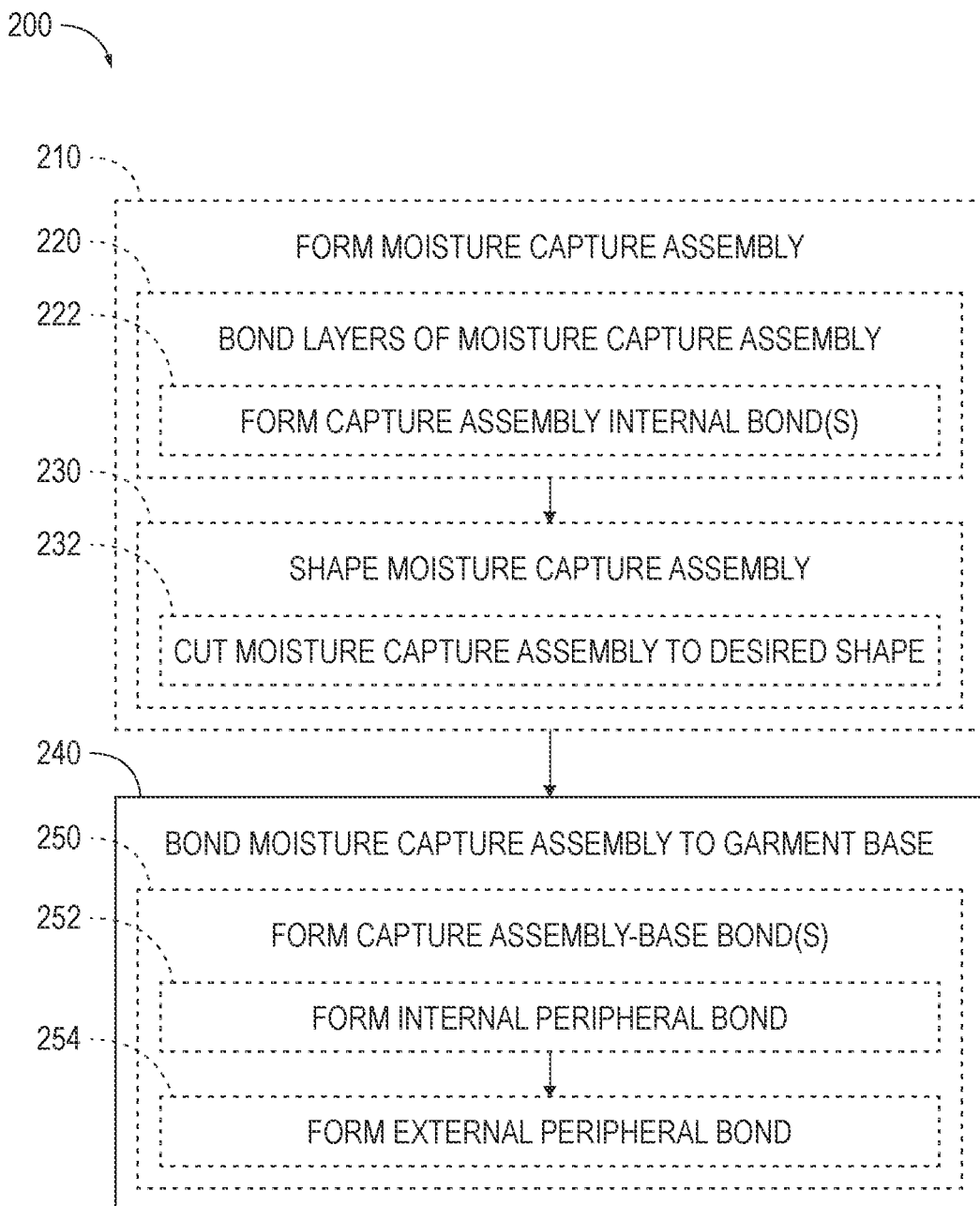
FIG. 11 is a flowchart depicting examples of methods of manufacturing a garment according to the present disclosure.

FIG. 11 is a flowchart depicting a method 200, according to the present disclosure, of manufacturing a garment, such as garment 10 disclosed herein. As shown in FIG. 11, method 200 includes bonding, at 240, a moisture capture assembly to a garment base. Examples of moisture capture assemblies and/or of garment bases that may be utilized in conjunction with methods 200 are disclosed herein with reference to moisture capture assembly 100 and/or garment base 80, respectively.

The bonding the moisture capture assembly to the garment base at 240 may be performed in any suitable manner according to the present disclosure. In particular, in some examples, and as shown in FIG. 11, the bonding the moisture capture assembly to the garment base at 240 includes forming, at 250, one or more capture assembly-base bonds to bond at least one base layer of the garment base and at least a portion of the moisture capture assembly to one another. In particular, in various examples, the bonding the moisture capture assembly to the garment base at 240 includes bonding the moisture capture assembly to the garment base using an adhesive bond (such as any suitable adhesive bond 60 disclosed herein) and/or without stitching and/or sewing. More specifically, in some examples, and as shown in FIG. 11, the forming the one or more capture assembly-base bonds at 250 includes forming, at 252, an internal peripheral bond and/or forming, at 254, an external peripheral bond. Examples of capture assembly-base bonds, of internal peripheral bonds, of external peripheral bonds, and/or of base layers that may be utilized in conjunction with methods 200 are disclosed herein with reference to capture assembly-base bond 64, internal peripheral bond 56, external peripheral bond 58, and/or any suitable base layer 82, respectively.

In some examples, the bonding the moisture capture assembly to the garment base at 240 includes bonding a pre-formed moisture capture assembly to the garment base. More specifically, in some examples, and as shown in FIG. 11, method 200 further includes, prior to the bonding the moisture capture assembly to the garment base at 240, forming, at 210, the moisture capture assembly.

The forming the moisture capture assembly at 210 may be performed in any suitable manner according to the present disclosure. In particular, in some examples, and as shown in FIG. 11, the forming the moisture capture assembly at 210 includes bonding, at 220, two or more layers of the moisture capture assembly to one another. More specifically, in examples, the bonding the two or more layers of the moisture capture assembly to one another at 220 may include bonding two or more of a moisture retention portion, an anti-leak portion, one or more moisture retention layers, a first moisture retention layer, a second moisture retention layer, a wicking layer, and/or a moisture barrier layer to one another. In some examples, and as shown in FIG. 11, the forming the moisture capture assembly at 210 and/or the bonding the two or more layers of the moisture capture assembly to one another at 220 includes forming, at 222, one or more capture assembly internal bonds. Examples of moisture retention portions, of anti-leak portions, of moisture retention layers, of first moisture retention layers, of second moisture retention layers, of wicking layers, of moisture barrier layers, and/or of capture assembly internal bonds that may be utilized in conjunction with methods 200 are disclosed herein with reference to moisture retention portion 120, anti-leak portion 130, moisture retention layer 124, first moisture retention layer 126, second moisture retention layer 128, wicking layer 110, moisture barrier layer 132, and/or capture assembly internal bond 66, respectively.

Additionally or alternatively, in some examples, and as shown in FIG. 11, the forming the moisture capture assembly at 210 includes shaping, at 230, the moisture capture assembly, such as to adapt the moisture capture assembly for incorporation with the garment base. In some examples, the shaping the moisture capture assembly at 230 is performed subsequent to the bonding the two or more layers of the moisture capture assembly to one another at 220. The shaping the moisture capture assembly at 230 may be performed in any of a variety of manners. As an example, and as shown in FIG. 11, the shaping the moisture capture assembly at 230 may include cutting, at 232, the moisture capture assembly to a desired shape, such as a shape corresponding to a crotch region of the garment. More specifically, in some such examples, the cutting the moisture capture assembly to the desired shape at 232 includes utilizing a die cutting process.

Illustrative, non-exclusive examples of inventive subject matter according to the present disclosure are described in the following enumerated paragraphs:

A1. A garment configured to be worn by a wearer, the garment comprising:
  a bonded region;
  a garment base; and
  a moisture capture assembly bonded to the garment base within the bonded region;
  wherein the moisture capture assembly includes:
    an assembly interior side that faces the wearer when the garment is worn by the wearer;
    an assembly exterior side that faces away from the wearer when the garment is worn by the wearer;
    a moisture retention portion configured to absorb and retain moisture from the wearer; and
    an anti-leak portion configured to restrict moisture from exiting the moisture retention portion; and
  wherein the moisture capture assembly is bonded to the garment base with a plurality of adhesive bonds formed within the bonded region.

A2. The garment of paragraph A1, wherein the plurality of adhesive bonds includes:
  an internal peripheral bond positioned on an interior side of at least a portion of the moisture capture assembly; and
  an external peripheral bond positioned on an exterior side of at least a portion of the moisture capture assembly.

A3. The garment of any of paragraphs A1-A2, further comprising a crotch region; wherein the moisture capture assembly is positioned at least partially within the crotch region.

A4. The garment of any of paragraphs A1-A3, wherein the garment base supports the moisture capture assembly, optionally within a/the crotch region.

A5. The garment of any of paragraphs A1-A4, wherein the plurality of adhesive bonds includes one or more capture assembly-base bonds; and wherein each capture assembly-base bond of the one or more capture assembly-base bonds operates to bond at least a portion of the moisture capture assembly to at least a portion of the garment base.

A6. The garment of paragraph A5, wherein the one or more capture assembly-base bonds includes one or both of an/the internal peripheral bond and an/the external peripheral bond.

A7. The garment of any of paragraphs A1-A6, wherein the plurality of adhesive bonds includes one or more capture assembly internal bonds; and wherein each capture assembly internal bond of the one or more capture assembly internal bonds operates to bond two or more distinct portions of the moisture capture assembly to one another.

A8. The garment of any of paragraphs A1-A7, wherein the plurality of adhesive bonds includes one or more base internal bonds; and wherein each base internal bond of the one or more base internal bonds operates to bond two or more distinct portions of the garment base to one another.

A9. The garment of paragraph A8, wherein the one or more base internal bonds includes one or both of an/the internal peripheral bond and an/the external peripheral bond.

A10. The garment of any of paragraphs A1-A9, wherein one or more adhesive bonds of the plurality of adhesive bonds are formed by an adhesive material that is applied to one or both of the garment base and the moisture capture assembly.

A11. The garment of paragraph A10, wherein the adhesive material includes one or more of a tape, an elastic tape, a film, an elastic film, a spray-on adhesive, and a thermoset adhesive.

A12. The garment of any of paragraphs A10-A11, wherein the adhesive material is one or more of water-resistant, water-repellent, and waterproof.

A13. The garment of any of paragraphs A1-A12, wherein one or more adhesive bonds of the plurality of adhesive bonds are formed at least partially via a thermocompression process.

A14. The garment of any of paragraphs A1-A13, wherein the garment includes a garment interior surface that faces the wearer when the garment is worn by the wearer and a garment exterior surface that faces away from the wearer when the garment is worn by the wearer.

A15. The garment of paragraph A14, wherein at least a portion of the garment interior surface is configured to directly contact the wearer when the garment is worn by the wearer.

A16. The garment of any of paragraphs A14-A15, wherein the garment is configured such that, when the garment is worn by the wearer, no portion of the garment is positioned directly between the garment interior surface and the wearer.

A17. The garment of any of paragraphs A14-A16, wherein the garment is configured such that, when the garment is worn by the wearer, no portion of the garment is positioned distal the wearer relative to the garment exterior surface.

A18. The garment of any of paragraphs A1-A17, wherein the garment includes a waistband region; and optionally wherein the garment base at least partially defines the waistband region.

A19. The garment of any of paragraphs A1-A18, wherein the garment defines one or more garment apertures; and optionally wherein the garment base at least partially defines the one or more garment apertures.

A20. The garment of paragraph A19, wherein at least one garment aperture of the one or more garment apertures defines a leg opening that is configured to receive a leg of the wearer when the garment is worn by the wearer.

A21. The garment of any of paragraphs A19-A20, further comprising an edge reinforcing strip positioned adjacent to at least one of the one or more garment apertures.

A22. The garment of paragraph A21, wherein the edge reinforcing strip is bonded to the garment base with at least one adhesive bond of the plurality of adhesive bonds.

A23. The garment of any of paragraphs A21-A22, wherein the edge reinforcing strip at least partially defines the at least one garment aperture; and optionally wherein the edge reinforcing strip at least partially defines a/the leg opening.

A24. The garment of any of paragraphs A21-A23, wherein the edge reinforcing strip is an elastic strip.

A25. The garment of any of paragraphs A1-A24, wherein the moisture capture assembly includes a moisture capture assembly central region and a moisture capture assembly peripheral region that circumferentially encloses the moisture capture assembly central region; and wherein the bonded region includes at least a portion of the moisture capture assembly peripheral region.

A26. The garment of any of paragraphs A1-A25, wherein the bonded region extends at least substantially or fully around a perimeter of a/the moisture capture assembly peripheral region.

A27. The garment of any of paragraphs A1-A26, wherein the garment base defines a garment lateral edge of the garment.

A28. The garment of paragraph A27, wherein the bonded region extends from a/the moisture capture assembly peripheral region toward, and optionally fully to, the garment lateral edge.

A29. The garment of any of paragraphs A27-A28, wherein a portion of the moisture capture assembly extends fully to the garment lateral edge.

A30. The garment of any of paragraphs A27-A28, wherein the moisture capture assembly includes and terminates at a moisture capture assembly lateral edge; optionally wherein the moisture capture assembly lateral edge defines the garment lateral edge or wherein the moisture capture assembly lateral edge does not define the garment lateral edge.

A31. The garment of any of paragraphs A27-A28, wherein the bonded region extends from a/the moisture capture assembly peripheral region to a point that is spaced apart from the garment lateral edge; and/or wherein the moisture capture assembly and the bonded region are spaced away from the garment lateral edge; and/or wherein the moisture capture assembly and the bonded region do not extend to the garment lateral edge.

A32. The garment of any of paragraphs A1-A31, wherein the moisture retention portion includes and terminates at a moisture retention portion lateral edge; and wherein the bonded region includes:

a laterally inward portion that extends from the moisture retention portion lateral edge toward a/the moisture capture assembly central region along a/the laterally inward direction; and a laterally outward portion that extends from the moisture retention portion lateral edge away from the moisture retention portion along a laterally outward direction that is opposite the laterally inward direction.

A33. The garment of any of paragraphs A1-A32, wherein the moisture capture assembly includes and terminates at a/the moisture capture assembly lateral edge; and wherein one of:

(i) the moisture capture assembly lateral edge is spaced apart from a/the moisture retention portion lateral edge along a/the laterally outward direction; or (ii) the moisture retention portion lateral edge defines the moisture capture assembly lateral edge.

A34. The garment of any of paragraphs A1-A33, wherein the garment base includes one or more base layers.

A35. The garment of paragraph A34, wherein at least one base layer of the one or more base layers and at least a portion of the moisture capture assembly are bonded to one another via at least one capture assembly-base bond of a/the one or more capture assembly-base bonds.

A36. The garment of paragraph A35, wherein the capture assembly-base bond is positioned only in a/the laterally inward portion of the bonded region.

A37. The garment of paragraph A35, wherein the capture assembly-base bond is positioned only in a/the laterally outward portion of the bonded region.

A38. The garment of paragraph A35, wherein the capture assembly-base bond extends within each of a/the laterally inward portion and a/the laterally outward portion of the bonded region.

A39. The garment of any of paragraphs A35-A38, wherein the capture assembly-base bond directly bonds the at least one base layer to the assembly interior side of the moisture capture assembly.

A40. The garment of any of paragraphs A35-A39, wherein the capture assembly-base bond directly bonds the at least one base layer to the assembly exterior side of the moisture capture assembly.

A41. The garment of any of paragraphs A34-A40, wherein each base layer of the one or more base layers includes and terminates at one or both of:

(i) a base layer lateral inward edge, such that the base layer extends away from the base layer lateral inward edge along a/the laterally outward direction; and (ii) a base layer lateral outward edge, such that the base layer extends away from the base layer lateral outward edge along a/the laterally inward direction.

A42. The garment of any of paragraphs A34-A41, wherein the one or more base layers includes an interior base layer that forms at least a portion of a/the garment interior surface.

A43. The garment of paragraph A42, wherein a/the base layer lateral inward edge of the interior base layer is spaced apart from a/the moisture retention portion lateral edge along a/the laterally inward direction.

A44. The garment of any of paragraphs A42-A43, wherein at least a portion of the interior base layer overlies at least a portion of the moisture capture assembly; optionally wherein at least a portion of the interior base layer overlies at least a portion of a/the moisture capture assembly peripheral region.

A45. The garment of any of paragraphs A42-A44, wherein a/the base layer lateral outward edge of the interior base layer is spaced apart from a/the moisture retention portion lateral edge along a/the laterally outward direction.

A46. The garment of any of paragraphs A42-A45, wherein the interior base layer extends within each of a/the laterally inward portion of the bonded region and a/the laterally outward portion of the bonded region.

A47. The garment of any of paragraphs A34-A46, wherein the one or more base layers includes an exterior base layer that forms at least a portion of a/the garment exterior surface.

A48. The garment of paragraph A47, wherein at least a portion of the exterior base layer underlies at least a portion of the moisture capture assembly; optionally wherein at least a portion of the exterior base layer underlies at least a portion of a/the moisture capture assembly peripheral region.

A49. The garment of paragraph A48, wherein at least a portion of the exterior base layer underlies at least a portion of a/the moisture capture assembly central region.

A50. The garment of any of paragraphs A47-A49, wherein a/the base layer lateral outward edge of the exterior base layer is spaced apart from a/the moisture retention portion lateral edge along a/the laterally outward direction.

A51. The garment of any of paragraphs A47-A50, wherein a/the base layer lateral outward edge of the exterior base layer is spaced apart from a/the moisture capture assembly lateral edge along a/the laterally outward direction.

A52. The garment of any of paragraphs A47-A51, wherein the exterior base layer extends within each of a/the laterally inward portion of the bonded region and a/the laterally outward portion of the bonded region.

A53. The garment of any of paragraphs A34-A52, wherein the one or more base layers includes an intermediate base layer that is positioned at least partially between one or both of:

(i) one other base layer of the one or more base layers and the moisture capture assembly; and (ii) two other base layers of the one or more base layers.

A54. The garment of paragraph A53, wherein a/the base layer lateral inward edge of the intermediate base layer is spaced apart from a/the moisture retention portion lateral edge along a/the laterally inward direction.

A55. The garment of any of paragraphs A53-A54, wherein at least a portion of the intermediate base layer underlies at least a portion of the moisture capture assembly; optionally wherein at least a portion of the intermediate base layer underlies at least a portion of a/the moisture capture assembly peripheral region.

A56. The garment of any of paragraphs A53-A55, wherein a/the base layer lateral outward edge of the intermediate base layer is spaced apart from a/the moisture retention portion lateral edge along a/the laterally outward direction.

A57. The garment of any of paragraphs A53-A56, wherein a/the base layer lateral outward edge of the intermediate base layer is spaced apart from a/the moisture capture assembly lateral edge along a/the laterally outward direction.

A58. The garment of any of paragraphs A53-A57, wherein the intermediate base layer extends within each of a/the laterally inward portion of the bonded region and a/the laterally outward portion of the bonded region.

A59. The garment of any of paragraphs A1-A58, wherein two or more of an/the interior base layer, an/the exterior base layer, and an/the intermediate base layer are bonded to one another via a/the base internal bond.

A60. The garment of paragraph A59, wherein the base internal bond is positioned only in a/the laterally inward portion of the bonded region.

A61. The garment of paragraph A59, wherein the base internal bond is positioned only in a/the laterally outward portion of the bonded region.

A62. The garment of paragraph A59, wherein the base internal bond extends within each of a/the laterally inward portion and a/the laterally outward portion of the bonded region.

A63. The garment of any of paragraphs A34-A62, wherein the one or more base layers includes an/the interior base layer and an/the intermediate base layer; and wherein a/the base layer lateral inward edge of the interior base layer is aligned with the base layer lateral inward edge of the intermediate base layer.

A64. The garment of any of paragraphs A34-A63, wherein the one or more base layers includes an/the interior base layer and an/the intermediate base layer; and wherein a/the base layer lateral inward edge of the interior base layer is spaced apart from the base layer lateral inward edge of the intermediate base layer along a/the laterally inward direction.

A65. The garment of any of paragraphs A34-A64, wherein the one or more base layers includes an/the interior base layer and an/the intermediate base layer; and wherein a/the base layer lateral inward edge of the interior base layer is spaced apart from the base layer lateral inward edge of the intermediate base layer along a/the laterally outward direction.

A66. The garment of any of paragraphs A34-A65, wherein the one or more base layers includes an/the interior base layer and an/the intermediate base layer; and wherein a/the base layer lateral outward edge of the interior base layer is aligned with the base layer lateral outward edge of the intermediate base layer.

A67. The garment of any of paragraphs A34-A66, wherein the one or more base layers includes an/the interior base layer and an/the intermediate base layer; and wherein a/the base layer lateral outward edge of the interior base layer is spaced apart from the base layer lateral outward edge of the intermediate base layer along a/the laterally inward direction.

A68. The garment of any of paragraphs A34-A67, wherein the one or more base layers includes an/the interior base layer and an/the intermediate base layer; and wherein a/the base layer lateral outward edge of the interior base layer is spaced apart from the base layer lateral outward edge of the intermediate base layer along a/the laterally outward direction.

A69. The garment of any of paragraphs A34-A68, wherein the one or more base layers includes an/the interior base layer and an/the intermediate base layer; and wherein the interior base layer and the intermediate base layer are directly bonded to one another via a/the base internal bond.

A70. The garment of any of paragraphs A34-A69, wherein the one or more base layers includes an/the interior base layer and an/the exterior base layer; and wherein a/the base layer lateral outward edge of the interior base layer is aligned with the base layer lateral outward edge of the exterior base layer.

A71. The garment of any of paragraphs A34-A70, wherein the one or more base layers includes an/the interior base layer and an/the exterior base layer; and wherein a/the base layer lateral outward edge of the interior base layer is spaced apart from the base layer lateral outward edge of the exterior base layer along a/the laterally inward direction.

A72. The garment of any of paragraphs A34-A71, wherein the one or more base layers includes an/the interior base layer and an/the exterior base layer; and wherein a/the base layer lateral outward edge of the interior base layer is spaced apart from the base layer lateral outward edge of the exterior base layer along a/the laterally outward direction.

A73. The garment of any of paragraphs A34-A72, wherein the one or more base layers includes an/the interior base layer and an/the intermediate base layer; and wherein the interior base layer and the exterior base layer are directly bonded to one another via a/the base internal bond.

A74. The garment of any of paragraphs A34-A73, wherein the one or more base layers includes an/the exterior base layer and an/the intermediate base layer; and wherein a/the base layer lateral outward edge of the exterior base layer is aligned with the base layer lateral outward edge of the intermediate base layer.

A75. The garment of any of paragraphs A34-A674, wherein the one or more base layers includes an/the exterior base layer and an/the intermediate base layer; and wherein a/the base layer lateral outward edge of the exterior base layer is spaced apart from the base layer lateral outward edge of the intermediate base layer along a/the laterally inward direction.

A76. The garment of any of paragraphs A34-A75, wherein the one or more base layers includes an/the exterior base layer and an/the intermediate base layer; and wherein a/the base layer lateral outward edge of the exterior base layer is spaced apart from the base layer lateral outward edge of the intermediate base layer along a/the laterally outward direction.

A77. The garment of any of paragraphs A34-A76, wherein the one or more base layers includes an/the exterior base layer and an/the intermediate base layer; and wherein the exterior base layer and the intermediate base layer are directly bonded to one another via a/the base internal bond.

A78. The garment of any of paragraphs A1-A77, wherein the garment base includes a plurality of base panels that are operatively coupled to one another.

A79. The garment of paragraph A78, wherein each base panel of the plurality of base panels includes at least one base layer of a/the one or more base layers.

A80. The garment of any of paragraphs A78-A79, wherein two or more base panels of the plurality of base panels are operatively coupled to one another at least partially via stitching.

A81. The garment of any of paragraphs A1-A80, wherein the moisture retention portion includes one or more moisture retention layers.

A82. The garment of paragraph A81, wherein the one or more moisture retention layers includes a first moisture retention layer and a second moisture retention layer.

A83 The garment of paragraph A82, wherein each of the first moisture retention layer and the second moisture retention layer extends to a/the moisture retention portion lateral edge.

A84. The garment of any of paragraphs A82-A83, wherein the first moisture retention layer and the second moisture retention layer are operatively coupled to one another.

A85. The garment of paragraph A84, wherein the first moisture retention layer and the second moisture retention layer are bonded to one another via at least one of a/the one or more capture assembly internal bonds.

A86. The garment of paragraph A85, wherein the capture assembly internal bond is positioned only in a/the laterally inward portion of the bonded region.

A87. The garment of paragraph A85, wherein the capture assembly internal bond extends within each of a/the laterally inward portion and a/the laterally outward portion of the bonded region.

A88. The garment of any of paragraphs A82-A87, wherein the first moisture retention layer and the second moisture retention layer are at least partially formed of different materials.

A89. The garment of any of paragraphs A1-A88, wherein the moisture retention portion includes a wicking layer configured to wick moisture away from the wearer.

A90. The garment of paragraph A89, wherein the wicking layer extends within each of a/the moisture capture assembly central region and a/the moisture capture assembly peripheral region.

A91. The garment of any of paragraphs A89-A90, wherein the wicking layer includes and terminates at a wicking layer lateral edge.

A92. The garment of paragraph A91, wherein the wicking layer lateral edge is aligned with a/the moisture retention portion lateral edge.

A93. The garment of paragraph A91, wherein the wicking layer lateral edge is spaced apart from a/the moisture retention portion lateral edge along a/the laterally inward direction.

A94. The garment of paragraph A91, wherein the wicking layer lateral edge is spaced apart from a/the moisture retention portion lateral edge along a/the laterally outward direction.

A95. The garment of any of paragraphs A91-A94, wherein the wicking layer extends within each of a/the laterally inward portion of the bonded region and a/the laterally outward portion of the bonded region.

A96. The garment of any of paragraphs A91-A95, wherein the wicking layer lateral edge defines a/the moisture capture assembly lateral edge.

A97. The garment of any of paragraphs A91-A95, wherein the wicking layer lateral edge is spaced apart from a/the moisture capture assembly lateral edge along a/the laterally inward direction.

A98. The garment of any of paragraphs A89-A97, wherein the wicking layer is operatively coupled to the moisture retention portion; optionally to the first moisture retention layer.

A99. The garment of paragraph A98, wherein the wicking layer and the moisture retention portion are bonded to one another via at least one adhesive bond of the plurality of adhesive bonds; optionally via at least one capture assembly internal bond of a/the one or more capture assembly internal bonds.

A100. The garment of any of paragraphs A1-A99, wherein the anti-leak portion includes, and optionally is, a moisture barrier layer that is operatively coupled to the moisture retention portion.

A101. The garment of paragraph A100, wherein the moisture barrier layer is bonded to the moisture retention portion via at least one adhesive bond of the plurality of adhesive bonds; optionally via at least one capture assembly internal bond of a/the one or more capture assembly internal bonds.

A102. The garment of any of paragraphs A100-A101, wherein the moisture barrier layer includes and terminates at a moisture barrier layer lateral edge.

A103. The garment of paragraph A102, wherein the moisture barrier layer lateral edge is aligned with a/the moisture retention portion lateral edge.

A104. The garment of paragraph A102, wherein the moisture barrier layer lateral edge is spaced apart from a/the moisture retention portion lateral edge along a/the laterally inward direction.

A105. The garment of paragraph A102, wherein the moisture barrier layer lateral edge is spaced apart from a/the moisture retention portion lateral edge along a/the laterally outward direction.

A106. The garment of any of paragraphs A100-A105, wherein the moisture barrier layer extends within each of a/the laterally inward portion of the bonded region and a/the laterally outward portion of the bonded region.

A107. The garment of any of paragraphs A100-A106, wherein a/the moisture barrier layer lateral edge defines a/the moisture capture assembly lateral edge.

A108. The garment of any of paragraphs A100-A106, wherein a/the moisture barrier layer lateral edge is spaced apart from a/the moisture capture assembly lateral edge along a/the laterally inward direction.

A109. The garment of any of paragraphs A1-A108, wherein the anti-leak portion includes, and optionally is, one or both of a moisture barrier treatment and a moisture barrier film that is applied to the moisture retention portion.

A110. The garment of any of paragraphs A1-A109, wherein at least one adhesive bond of the plurality of adhesive bonds is each of a/the capture assembly-base bond and a/the capture assembly internal bond.

A111. The garment of any of paragraphs A1-A110, wherein at least one adhesive bond of the plurality of adhesive bonds is each of a/the capture assembly-base bond and a/the base internal bond.

A112. The garment of any of paragraphs A1-A111, wherein at least one adhesive bond of the plurality of adhesive bonds is each of a/the capture assembly internal bond and a/the base internal bond.

A113. The garment of any of paragraphs A1-A112, wherein a/the one or more base layers includes an/the interior base layer; and wherein the interior base layer and the moisture retention portion are directly bonded to one another via a/the capture assembly-base bond.

A114. The garment of any of paragraphs A1-A113, wherein a/the one or more base layers includes an/the interior base layer; and wherein a/the base layer lateral inward edge of the interior base layer is spaced apart from a/the moisture capture assembly lateral edge along a/the laterally inward direction.

A115. The garment of any of paragraphs A1-A114, wherein a/the one or more base layers includes an/the interior base layer; and wherein the interior base layer overlies at least a portion of the moisture capture assembly within one or both of a/the moisture capture assembly peripheral region and a/the laterally inward portion of the bonded region.

A116. The garment of any of paragraphs A1-A115, wherein a/the one or more base layers includes an/the interior base layer; and wherein a/the base layer lateral outward edge of the interior base layer is aligned with a/the moisture capture assembly lateral edge.

A117. The garment of any of paragraphs A1-A116, wherein a/the one or more base layers includes an/the interior base layer; and wherein a/the base layer lateral outward edge of the interior base layer is spaced apart from a/the moisture capture assembly lateral edge along a/the laterally inward direction.

A118. The garment of any of paragraphs A1-A117, wherein a/the one or more base layers includes an/the interior base layer; and wherein a/the base layer lateral outward edge of the interior base layer is spaced apart from a/the moisture capture assembly lateral edge along a/the laterally outward direction.

A119. The garment of any of paragraphs A1-A118, wherein a/the one or more base layers includes an/the interior base layer; wherein the moisture retention portion includes a/the wicking layer; and wherein the interior base layer and the wicking layer are directly bonded to one another via a/the capture assembly-base bond.

A120. The garment of any of paragraphs A1-A119, wherein a/the one or more base layers includes an/the interior base layer; wherein the moisture retention portion includes a/the wicking layer; and wherein a/the base layer lateral inward edge of the interior base layer is spaced apart from a/the wicking layer lateral edge along a/the laterally inward direction.

A121. The garment of any of paragraphs A1-A120, wherein a/the one or more base layers includes an/the interior base layer; wherein the moisture retention portion includes a/the wicking layer; and wherein the interior base layer overlies at least a portion of the wicking layer within one or both of a/the moisture capture assembly peripheral region and a/the laterally inward portion of the bonded region.

A122. The garment of any of paragraphs A1-A121, wherein a/the one or more base layers includes an/the interior base layer; wherein the moisture retention portion includes a/the wicking layer; and wherein a/the base layer lateral outward edge of the interior base layer is aligned with a/the wicking layer lateral edge.

A123. The garment of any of paragraphs A1-A122, wherein a/the one or more base layers includes an/the interior base layer; wherein the moisture retention portion includes a/the wicking layer; and wherein a/the base layer lateral outward edge of the interior base layer is spaced apart from a/the wicking layer lateral edge along a/the laterally outward direction.

A124. The garment of any of paragraphs A1-A123, wherein a/the one or more base layers includes an/the interior base layer; wherein the anti-leak portion includes a/the moisture barrier layer; and wherein the interior base layer and the moisture barrier layer are directly bonded to one another via a/the capture assembly-base bond.

A125. The garment of any of paragraphs A1-A124, wherein a/the one or more base layers includes an/the interior base layer; wherein the anti-leak portion includes a/the moisture barrier layer; and wherein a/the base layer lateral inward edge of the interior base layer is spaced apart from a/the moisture barrier layer lateral edge along a/the laterally inward direction.

A126. The garment of any of paragraphs A1-A125, wherein a/the one or more base layers includes an/the interior base layer; wherein the anti-leak portion includes a/the moisture barrier layer; and wherein the interior base layer overlies at least a portion of the moisture barrier layer within one or both of a/the moisture capture assembly peripheral region and a/the laterally inward portion of the bonded region.

A127. The garment of any of paragraphs A1-A126, wherein a/the one or more base layers includes an/the interior base layer; wherein the anti-leak portion includes a/the moisture barrier layer; and wherein the interior base layer overlies at least a portion of the moisture barrier layer within a/the laterally outward portion of the bonded region.

A128. The garment of any of paragraphs A1-A127, wherein a/the one or more base layers includes an/the interior base layer; wherein the anti-leak portion includes a/the moisture barrier layer; and wherein a/the base layer lateral outward edge of the interior base layer is aligned with a/the moisture barrier layer lateral edge.

A129. The garment of any of paragraphs A1-A128, wherein a/the one or more base layers includes an/the interior base layer; wherein the anti-leak portion includes a/the moisture barrier layer; and wherein a/the base layer lateral outward edge of the interior base layer is spaced apart from a/the moisture barrier layer lateral edge along a/the laterally inward direction.

A130. The garment of any of paragraphs A1-A129, wherein a/the one or more base layers includes an/the interior base layer; wherein the anti-leak portion includes a/the moisture barrier layer; and wherein a/the base layer lateral outward edge of the interior base layer is spaced apart from a/the moisture barrier layer lateral edge along a/the laterally outward direction.

A131. The garment of any of paragraphs A1-A130, wherein a/the one or more base layers includes an/the intermediate base layer; and wherein the intermediate base layer and the moisture retention portion are directly bonded to one another via a/the capture assembly-base bond.

A132. The garment of any of paragraphs A1-A131, wherein a/the one or more base layers includes an/the intermediate base layer; and wherein a/the base layer lateral inward edge of the intermediate base layer is spaced apart from a/the moisture capture assembly lateral edge along a/the laterally inward direction.

A133. The garment of any of paragraphs A1-A132, wherein a/the one or more base layers includes an/the intermediate base layer; and wherein the intermediate base layer underlies at least a portion of the moisture capture assembly within one or both of a/the moisture capture assembly peripheral region and a/the laterally inward portion of the bonded region.

A134. The garment of any of paragraphs A1-A133, wherein a/the one or more base layers includes an/the intermediate base layer; and wherein a/the base layer lateral outward edge of the intermediate base layer is aligned with a/the moisture capture assembly lateral edge.

A135. The garment of any of paragraphs A1-A134, wherein a/the one or more base layers includes an/the intermediate base layer; and wherein a/the base layer lateral outward edge of the intermediate base layer is spaced apart from a/the moisture capture assembly lateral edge along a/the laterally inward direction.

A136. The garment of any of paragraphs A1-A135, wherein a/the one or more base layers includes an/the intermediate base layer; and wherein a/the base layer lateral outward edge of the intermediate base layer is spaced apart from a/the moisture capture assembly lateral edge along a/the laterally outward direction.

A137. The garment of any of paragraphs A1-A136, wherein a/the one or more base layers includes an/the intermediate base layer; wherein the moisture retention portion includes a/the wicking layer; and wherein the intermediate base layer and the wicking layer are directly bonded to one another via a/the capture assembly-base bond.

A138. The garment of any of paragraphs A1-A137, wherein a/the one or more base layers includes an/the intermediate base layer; wherein the moisture retention portion includes a/the wicking layer; and wherein a/the base layer lateral inward edge of the intermediate base layer is spaced apart from a/the wicking layer lateral edge along a/the laterally inward direction.

A139. The garment of any of paragraphs A1-A138, wherein a/the one or more base layers includes an/the intermediate base layer; wherein the moisture retention portion includes a/the wicking layer; and wherein the intermediate base layer underlies at least a portion of the wicking layer within one or both of a/the moisture capture assembly peripheral region and a/the laterally inward portion of the bonded region.

A140. The garment of any of paragraphs A1-A139, wherein a/the one or more base layers includes an/the intermediate base layer; wherein the moisture retention portion includes a/the wicking layer; and wherein a/the base layer lateral outward edge of the intermediate base layer is aligned with a/the wicking layer lateral edge.

A141. The garment of any of paragraphs A1-A140, wherein a/the one or more base layers includes an/the intermediate base layer; wherein the moisture retention portion includes a/the wicking layer; and wherein a/the base layer lateral outward edge of the intermediate base layer is spaced apart from a/the wicking layer lateral edge along a/the laterally inward direction.

A142. The garment of any of paragraphs A1-A141, wherein a/the one or more base layers includes an/the intermediate base layer; wherein the moisture retention portion includes a/the wicking layer; and wherein a/the base layer lateral outward edge of the intermediate base layer is spaced apart from a/the wicking layer lateral edge along a/the laterally outward direction.

A143. The garment of any of paragraphs A1-A142, wherein a/the one or more base layers includes an/the intermediate base layer; wherein the anti-leak portion includes a/the moisture barrier layer; and wherein the intermediate base layer and the moisture barrier layer are directly bonded to one another via a/the capture assembly-base bond.

A144. The garment of any of paragraphs A1-A143, wherein a/the one or more base layers includes an/the intermediate base layer; wherein the anti-leak portion includes a/the moisture barrier layer; and wherein a/the base layer lateral inward edge of the intermediate base layer is spaced apart from a/the moisture barrier layer lateral edge along a/the laterally inward direction.

A145. The garment of any of paragraphs A1-A144, wherein a/the one or more base layers includes an/the intermediate base layer; wherein the anti-leak portion includes a/the moisture barrier layer; and wherein the intermediate base layer underlies at least a portion of the moisture barrier layer within one or both of a/the moisture capture assembly peripheral region and a/the laterally inward portion of the bonded region.

A146. The garment of any of paragraphs A1-A145, wherein a/the one or more base layers includes an/the intermediate base layer; wherein the anti-leak portion includes a/the moisture barrier layer; and wherein the intermediate base layer underlies at least a portion of the moisture barrier layer within a/the laterally outward portion of the bonded region.

A147. The garment of any of paragraphs A1-A146, wherein a/the one or more base layers includes an/the intermediate base layer; wherein the anti-leak portion includes a/the moisture barrier layer; and wherein a/the base layer lateral outward edge of the intermediate base layer is aligned with a/the moisture barrier layer lateral edge.

A148. The garment of any of paragraphs A1-A147, wherein a/the one or more base layers includes an/the intermediate base layer; wherein the anti-leak portion includes a/the moisture barrier layer; and wherein a/the base layer lateral outward edge of the intermediate base layer is spaced apart from a/the moisture barrier layer lateral edge along a/the laterally inward direction.

A149. The garment of any of paragraphs A1-A148, wherein a/the one or more base layers includes an/the intermediate base layer; wherein the anti-leak portion includes a/the moisture barrier layer; and wherein a/the base layer lateral outward edge of the intermediate base layer is spaced apart from a/the moisture barrier layer lateral edge along a/the laterally outward direction.

A150. The garment of any of paragraphs A1-A149, wherein a/the one or more base layers includes an/the exterior base layer; and wherein the exterior base layer and the moisture retention portion are directly bonded to one another via a/the capture assembly-base bond.

A151. The garment of any of paragraphs A1-A150, wherein a/the one or more base layers includes an/the exterior base layer; and wherein the exterior base layer underlies at least a portion of the moisture capture assembly within one or both of a/the moisture capture assembly peripheral region and a/the laterally inward portion of the bonded region.

A152. The garment of any of paragraphs A1-A151, wherein a/the one or more base layers includes an/the exterior base layer; and wherein a/the base layer lateral outward edge of the exterior base layer is aligned with a/the moisture capture assembly lateral edge.

A153. The garment of any of paragraphs A1-A152, wherein a/the one or more base layers includes an/the exterior base layer; and wherein a/the base layer lateral outward edge of the exterior base layer is spaced apart from a/the moisture capture assembly lateral edge along a/the laterally inward direction.

A154. The garment of any of paragraphs A1-A153, wherein a/the one or more base layers includes an/the exterior base layer; and wherein a/the base layer lateral outward edge of the exterior base layer is spaced apart from a/the moisture capture assembly lateral edge along a/the laterally outward direction.

A155. The garment of any of paragraphs A1-A154, wherein a/the one or more base layers includes an/the exterior base layer; wherein the moisture retention portion includes a/the wicking layer; and wherein the exterior base layer and the wicking layer are directly bonded to one another via a/the capture assembly-base bond.

A156. The garment of any of paragraphs A1-A155, wherein a/the one or more base layers includes an/the exterior base layer; wherein the moisture retention portion includes a/the wicking layer; and wherein the exterior base layer underlies at least a portion of the wicking layer within one or both of a/the moisture capture assembly peripheral region and a/the laterally inward portion of the bonded region.

A157. The garment of any of paragraphs A1-A156, wherein a/the one or more base layers includes an/the exterior base layer; wherein the moisture retention portion includes a/the wicking layer; and wherein a/the base layer lateral outward edge of the exterior base layer is aligned with a/the wicking layer lateral edge.

A158. The garment of any of paragraphs A1-A157, wherein a/the one or more base layers includes an/the exterior base layer; wherein the moisture retention portion includes a/the wicking layer; and wherein a/the base layer lateral outward edge of the exterior base layer is spaced apart from a/the wicking layer lateral edge along a/the laterally inward direction.

A159. The garment of any of paragraphs A1-A158, wherein a/the one or more base layers includes an/the exterior base layer; wherein the moisture retention portion includes a/the wicking layer; and wherein a/the base layer lateral outward edge of the exterior base layer is spaced apart from a/the wicking layer lateral edge along a/the laterally outward direction.

A160. The garment of any of paragraphs A1-A159, wherein a/the one or more base layers includes an/the exterior base layer; wherein the anti-leak portion includes a/the moisture barrier layer; and wherein the exterior base layer and the moisture barrier layer are directly bonded to one another via a/the capture assembly-base bond.

A161. The garment of any of paragraphs A1-A160, wherein a/the one or more base layers includes an/the exterior base layer; wherein the anti-leak portion includes a/the moisture barrier layer; and wherein the exterior base layer underlies at least a portion of the moisture barrier layer within one or both of a/the moisture capture assembly peripheral region and a/the laterally inward portion of the bonded region.

A162. The garment of any of paragraphs A1-A161, wherein a/the one or more base layers includes an/the exterior base layer; wherein the anti-leak portion includes a/the moisture barrier layer; and wherein the exterior base layer underlies at least a portion of the moisture barrier layer within a/the laterally outward portion of the bonded region.

A163. The garment of any of paragraphs A1-A162, wherein a/the one or more base layers includes an/the exterior base layer; wherein the anti-leak portion includes a/the moisture barrier layer;

and wherein a/the base layer lateral outward edge of the exterior base layer is aligned with a/the moisture barrier layer lateral edge.

A164. The garment of any of paragraphs A1-A163, wherein a/the one or more base layers includes an/the exterior base layer; wherein the anti-leak portion includes a/the moisture barrier layer; and wherein a/the base layer lateral outward edge of the exterior base layer is spaced apart from a/the moisture barrier layer lateral edge along a/the laterally inward direction.

A165. The garment of any of paragraphs A1-A164, wherein a/the one or more base layers includes an/the exterior base layer; wherein the anti-leak portion includes a/the moisture barrier layer; and wherein a/the base layer lateral outward edge of the exterior base layer is spaced apart from a/the moisture barrier layer lateral edge along a/the laterally outward direction.

A166. The garment of any of paragraphs A1-A165, wherein one or more of the garment base, a/the one or more base layers, an/the interior base layer, an/the exterior base layer, and an/the interior base layer is at least partially formed of one or more of a natural fiber, cotton, a synthetic fiber, polyester, nylon, Spandex™ fabric, and combinations thereof.

A167. The garment of any of paragraphs A1-A166, wherein one or more of the moisture capture assembly, a/the moisture retention portion, a/the first moisture retention layer, a/the second moisture retention layer, a/the wicking layer, and a/the moisture barrier layer is at least partially formed of one or more of a natural fiber, cotton, a synthetic fiber, polyester, nylon, Spandex™ fabric, and combinations thereof.

A168. The garment of any of paragraphs A1-A167, wherein the garment is an undergarment.

A169. The garment of any of paragraphs A1-A168, wherein the garment is an outerwear garment.

A170. The garment of any of paragraphs A1-A169, wherein the garment is a short.

A171. The garment of any of paragraphs A1-A170, wherein the garment is an activewear garment.

A172. The garment of any of paragraphs A1-A171, wherein the garment is configured to be washed and re-worn numerous times.

B1. A garment configured to be worn by a wearer and to be washed and re-worn numerous times, the garment comprising:
  a plurality of adhesive bonds within a bonded region of the garment;
  a garment base, wherein the garment base defines a garment lateral edge of the garment; and
  a moisture capture assembly bonded to the garment base within the bonded region of the garment by at least a subset of the plurality of adhesive bonds, wherein the moisture capture assembly has a perimeter, an assembly interior side that faces the wearer when the garment is worn by the wearer, and an assembly exterior side that faces away from the wearer when the garment is worn by the wearer, and wherein the moisture capture assembly comprises at least:
    a moisture retention portion configured to absorb and retain moisture from the wearer; and
    an anti-leak portion configured to restrict moisture from exiting the moisture retention portion and positioned toward the assembly exterior side of the moisture capture assembly relative to the moisture retention portion;
  wherein the bonded region extends fully around the perimeter of the moisture capture assembly, and wherein the moisture capture assembly and the bonded region do not extend to the garment lateral edge.

B2. The garment of paragraph B1, wherein the moisture capture assembly is positioned at least partially within a crotch region of the garment, and wherein the garment lateral edge comprises a leg opening of the garment.

B3. The garment of any of paragraphs B1-B2, wherein the plurality of adhesive bonds comprises:
  an internal peripheral bond positioned on the assembly interior side and that operates to bond the moisture capture assembly to the garment base; and
  an external peripheral bond positioned on the assembly exterior side and that operates to bond the moisture capture assembly to the garment base.

B4. The garment of paragraph B3, wherein the plurality of adhesive bonds further comprises one or more capture assembly internal bonds, and wherein each capture assembly internal bond of the one or more capture assembly internal bonds operates to bond two or more distinct portions of the moisture capture assembly to one another.

B5. The garment of paragraph B4,
  wherein the moisture retention portion includes:
    a wicking layer that comprises the assembly interior side and is configured to wick moisture away from the wearer; and
    one or more moisture retention layers between the wicking layer and the anti-leak portion; and
  wherein the one or more capture assembly internal bonds operate to bond the wicking layer to a moisture retention layer of the one or more moisture retention layers.

B6. The garment of paragraph B5, wherein the one or more moisture retention layers comprises two moisture retention layers positioned between the wicking layer and the anti-leak portion, and wherein the one or more capture assembly internal bonds further operate to bond the two moisture retention layers to one another.

B7. The garment of paragraph B6, wherein the two moisture retention layers are formed of different materials.

B8. The garment of any of paragraphs B5-B7, wherein the anti-leak portion comprises a moisture barrier layer, and wherein the one or more capture assembly internal bonds further operate to bond the moisture barrier layer to the one or more moisture retention layers.

B9. The garment of paragraph B8, wherein the moisture barrier layer comprises a moisture barrier layer lateral edge, wherein the moisture retention portion comprises a moisture retention portion lateral edge, and wherein the moisture barrier layer lateral edge is spaced laterally outward from the moisture retention portion lateral edge.

B10. The garment of paragraph B9,
  wherein the garment base comprises a plurality of base layers comprising an interior base layer and at least one other base layer; and
  wherein the internal peripheral bond further operates to bond the interior base layer to the wicking layer and to the moisture barrier layer.

B11. The garment of paragraph B10, wherein the at least one other base layer comprises an intermediate base layer and an exterior base layer, wherein the internal peripheral bond further operates to bond the interior base layer to the intermediate base layer, wherein the intermediate base layer at least partially defines the garment lateral edge, and wherein a base layer lateral outward edge of the exterior base layer is spaced away from the garment lateral edge.

B12. The garment of paragraph B11, wherein the exterior base layer is coextensive with the moisture capture assembly.

B13. The garment of any of paragraphs B10-B12, wherein the interior base layer is a closed structure that coincides with the bonded region.

B14. The garment of any of paragraphs B5-B13, wherein the anti-leak portion comprises a moisture barrier treatment applied to a moisture retention layer of the one or more moisture retention layers.

B15. The garment of any of paragraphs B1-B14, further comprising the subject matter of any of paragraphs A1-A172.

C1. A garment configured to be worn by a wearer and to be washed and re-worn numerous times, the garment comprising:

a garment base comprising an interior base layer and at least one other base layer, wherein the garment base defines a garment lateral edge of the garment, and wherein the garment base defines a pair of leg openings;

a moisture capture assembly bonded to the garment base within a bonded region of the garment, wherein the moisture capture assembly has a perimeter, an assembly interior side that faces the wearer when the garment is worn by the wearer, and an assembly exterior side that faces away from the wearer when the garment is worn by the wearer, wherein the bonded region extends fully around the perimeter of the moisture capture assembly, wherein the moisture capture assembly and the bonded region do not extend to the leg openings, wherein the moisture capture assembly is positioned at least partially within a crotch region of the garment, and wherein the moisture capture assembly comprises at least:

a wicking layer that comprises the assembly interior side and is configured to wick moisture away from the wearer;

a moisture retention portion configured to absorb and retain moisture from the wearer and comprising one or more moisture retention layers, wherein the moisture retention portion comprises a moisture retention portion lateral edge; and a moisture barrier layer configured to restrict moisture from exiting the moisture retention portion, wherein the one or more moisture retention layers are positioned between the wicking layer and the moisture barrier layer, and wherein the moisture barrier layer comprises a moisture barrier layer lateral edge that is spaced laterally outward from the moisture retention portion lateral edge; and a plurality of adhesive bonds within the bonded region of the garment, wherein the plurality of adhesive bonds comprises:

an internal peripheral bond positioned on the assembly interior side and that operates to bond the moisture capture assembly to the garment base, and to bond the interior base layer to the wicking layer and to the moisture barrier layer;

an external peripheral bond positioned on the assembly exterior side and that operates to bond the moisture capture assembly to the garment base; and one or more capture assembly internal bonds that operate to bond the wicking layer to the one or more moisture retention layers, and to bond the moisture barrier layer to the one or more moisture retention layers;

wherein the interior base layer is a closed structure that coincides with the bonded region.

C2. The garment of paragraph C1, wherein the at least one other base layer comprises an intermediate base layer and an exterior base layer, wherein the internal peripheral bond further operates to bond the interior base layer to the intermediate base layer, wherein the intermediate base layer at least partially defines the garment lateral edge, and wherein a base layer lateral outward edge of the exterior base layer is spaced away from the garment lateral edge.

C3. The garment of paragraph C2, wherein the exterior base layer is coextensive with the moisture capture assembly.

C4. The garment of any of paragraphs C1-C3, wherein the one or more moisture retention layers comprises two moisture retention layers positioned between the wicking layer and the moisture barrier layer, and wherein the one or more capture assembly internal bonds further operate to bond the two moisture retention layers to one another.

C5. The garment of any of paragraphs C1-C4, further comprising the subject matter of any of paragraphs A1-A172.

D1. A method of manufacturing the garment of any of paragraphs A1-C5, the method comprising:

bonding, with the plurality of adhesive bonds, the moisture capture assembly to the garment base.

D2. The method of paragraph D1, wherein the bonding the moisture capture assembly to the garment base includes forming a/the one or more capture assembly-base bonds to bond at least one base layer of a/the one or more base layers and at least a portion of the moisture capture assembly to one another.

D3. The method of paragraph D2, wherein the forming the one or more capture assembly-base bonds includes forming an/the internal peripheral bond.

D4. The method of any of paragraphs D2-D3, wherein the forming the one or more capture assembly-base bonds includes forming an/the external peripheral bond.

D5. The method of any of paragraphs D1-D4, further comprising, prior to the bonding the moisture capture assembly to the garment base, forming the moisture capture assembly.

D6. The method of paragraph D5, wherein the forming the moisture capture assembly includes bonding two or more layers of the moisture capture assembly to one another; optionally wherein the two or more layers of the moisture capture assembly include two or more of the moisture retention portion, the anti-leak portion, a/the one or more moisture retention layers, a/the first moisture retention layer, a/the second moisture retention layer, a/the wicking layer, and the moisture barrier layer.

D7. The method of any of paragraphs D5-D6, wherein the forming the moisture capture assembly includes forming a/the one or more capture assembly internal bonds.

D8. The method of any of paragraphs D5-D7, wherein the forming the moisture capture assembly includes shaping the moisture capture assembly.

D9. The method of paragraph D8, when dependent from paragraph B6, wherein the shaping the moisture capture assembly is performed subsequent to the bonding the two or more layers of the moisture capture assembly to one another.

D10. The method of any of paragraphs D8-D9, wherein the moisture capture assembly includes cutting the moisture capture assembly to a desired shape.

D11. The method of paragraph D10, wherein the cutting the moisture capture assembly to the desired shape includes die cutting.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa. Similarly, subject matter that is recited as being configured to perform a particular function may additionally or alternatively be described as being operative to perform that function.

As used herein, the term "and/or" placed between a first entity and a second entity means one of (1) the first entity, (2) the second entity, and (3) the first entity and the second entity. Multiple entries listed with "and/or" should be construed in the same manner, i.e., "one or more" of the entities so conjoined. Other entities optionally may be present other than the entities specifically identified by the "and/or" clause, whether related or unrelated to those entities specifically identified. Thus, as a non-limiting example, a reference to "A and/or B," when used in conjunction with open-ended language such as "comprising," may refer, in one example, to A only (optionally including entities other than B); in another example, to B only (optionally including entities other than A); in yet another example, to both A and B (optionally including other entities). These entities may refer to elements, actions, structures, steps, operations, values, and the like.

As used herein, the phrase "at least one," in reference to a list of one or more entities should be understood to mean at least one entity selected from any one or more of the entities in the list of entities, but not necessarily including at least one of each and every entity specifically listed within the list of entities and not excluding any combinations of entities in the list of entities. This definition also allows that entities may optionally be present other than the entities specifically identified within the list of entities to which the phrase "at least one" refers, whether related or unrelated to those entities specifically identified. Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including entities other than B); in another embodiment, to at least one, optionally including more than one, B, with no A present (and optionally including entities other than A); in yet another embodiment, to at least one, optionally including more than one, A, and at least one, optionally including more than one, B (and optionally including other entities). In other words, the phrases "at least one," "one or more," and "and/or" are open-ended expressions that are both conjunctive and disjunctive in operation. For example, each of the expressions "at least one of A, B, and C," "at least one of A, B, or C," "one or more of A, B, and C," "one or more of A, B, or C," and "A, B, and/or C" may mean A alone, B alone, C alone, A and B together, A and C together, B and C together, A, B, and C together, and optionally any of the above in combination with at least one other entity.

As used herein, the phrase "at least substantially," when modifying a degree or relationship, includes not only the recited "substantial" degree or relationship, but also the full extent of the recited degree or relationship. A substantial amount of a recited degree or relationship may include at least 75% of the recited degree or relationship. For example, a first component that extends at least substantially around a second component includes a first component that extends around at least 75% of a circumference of the second component and also includes a first component that extends fully circumferentially around the second component.

As used herein, the phrase, "for example," the phrase, "as an example," and/or simply the term "example," when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

The various disclosed elements of apparatuses disclosed herein are not required to all apparatuses according to the present disclosure, and the present disclosure includes all novel and non-obvious combinations and subcombinations of the various elements disclosed herein. Moreover, one or more of the various elements disclosed herein may define independent inventive subject matter that is separate and apart from the whole of a disclosed apparatus. Accordingly, such inventive subject matter is not required to be associated with the specific apparatuses that are expressly disclosed herein, and such inventive subject matter may find utility in apparatuses and/or methods that are not expressly disclosed herein.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, when the disclosure or subsequently filed claims recite "a" or "a first" element or the equivalent thereof, such disclosure and/or claims should be understood to include incorporation of one or more such elements, neither requiring nor excluding two or more such elements.

The invention claimed is:

1. A garment configured to be worn by a wearer and to be washed and re-worn numerous times, the garment comprising:
   a plurality of adhesive bonds within a bonded region of the garment;
   a garment base, wherein the garment base defines a garment lateral edge of the garment; and
   a moisture capture assembly bonded to the garment base within the bonded region of the garment by at least a subset of the plurality of adhesive bonds, wherein the moisture capture assembly has a perimeter, an assembly interior side that faces the wearer when the garment is worn by the wearer, and an assembly exterior side that faces away from the wearer when the garment is worn by the wearer, and wherein the moisture capture assembly comprises at least:
      a moisture retention portion configured to absorb and retain moisture from the wearer; and
      an anti-leak portion configured to restrict moisture from exiting the moisture retention portion and positioned toward the assembly exterior side of the moisture capture assembly relative to the moisture retention portion;
   wherein the bonded region extends fully around the perimeter of the moisture capture assembly, and wherein the moisture capture assembly and the bonded region do not extend to the garment lateral edge.

2. The garment of claim 1, wherein the moisture capture assembly is positioned at least partially within a crotch region of the garment, and wherein the garment lateral edge comprises a leg opening of the garment.

3. The garment of claim 1, wherein the plurality of adhesive bonds comprises:
an internal peripheral bond positioned on the assembly interior side and that operates to bond the moisture capture assembly to the garment base; and
an external peripheral bond positioned on the assembly exterior side and that operates to bond the moisture capture assembly to the garment base.

4. The garment of claim 3, wherein the plurality of adhesive bonds further comprises one or more capture assembly internal bonds, and wherein each capture assembly internal bond of the one or more capture assembly internal bonds operates to bond two or more distinct portions of the moisture capture assembly to one another.

5. The garment of claim 4,
wherein the moisture retention portion includes:
a wicking layer that comprises the assembly interior side and is configured to wick moisture away from the wearer; and
one or more moisture retention layers between the wicking layer and the anti-leak portion; and
wherein the one or more capture assembly internal bonds operate to bond the wicking layer to a moisture retention layer of the one or more moisture retention layers.

6. The garment of claim 5, wherein the one or more moisture retention layers comprises two moisture retention layers positioned between the wicking layer and the anti-leak portion, and wherein the one or more capture assembly internal bonds further operate to bond the two moisture retention layers to one another.

7. The garment of claim 6, wherein the two moisture retention layers are formed of different materials.

8. The garment of claim 5, wherein the anti-leak portion comprises a moisture barrier layer, and wherein the one or more capture assembly internal bonds further operate to bond the moisture barrier layer to the one or more moisture retention layers.

9. The garment of claim 8, wherein the moisture barrier layer comprises a moisture barrier layer lateral edge, wherein the moisture retention portion comprises a moisture retention portion lateral edge, and wherein the moisture barrier layer lateral edge is spaced laterally outward from the moisture retention portion lateral edge.

10. The garment of claim 9,
wherein the garment base comprises a plurality of base layers comprising an interior base layer and at least one other base layer; and
wherein the internal peripheral bond further operates to bond the interior base layer to the wicking layer and to the moisture barrier layer.

11. The garment of claim 10, wherein the at least one other base layer comprises an intermediate base layer and an exterior base layer, wherein the internal peripheral bond further operates to bond the interior base layer to the intermediate base layer, wherein the intermediate base layer at least partially defines the garment lateral edge, and wherein a base layer lateral outward edge of the exterior base layer is spaced away from the garment lateral edge.

12. The garment of claim 11, wherein the exterior base layer is coextensive with the moisture capture assembly.

13. The garment of claim 10, wherein the interior base layer is a closed structure that coincides with the bonded region.

14. The garment of claim 5, wherein the anti-leak portion comprises a moisture barrier treatment applied to a moisture retention layer of the one or more moisture retention layers.

15. A garment configured to be worn by a wearer and to be washed and re-worn numerous times, the garment comprising:
a garment base comprising an interior base layer and at least one other base layer, wherein the garment base defines a garment lateral edge of the garment, and wherein the garment base defines a pair of leg openings;
a moisture capture assembly bonded to the garment base within a bonded region of the garment, wherein the moisture capture assembly has a perimeter, an assembly interior side that faces the wearer when the garment is worn by the wearer, and an assembly exterior side that faces away from the wearer when the garment is worn by the wearer, wherein the bonded region extends fully around the perimeter of the moisture capture assembly, wherein the moisture capture assembly and the bonded region do not extend to the leg openings, wherein the moisture capture assembly is positioned at least partially within a crotch region of the garment, and wherein the moisture capture assembly comprises at least:
a wicking layer that comprises the assembly interior side and is configured to wick moisture away from the wearer;
a moisture retention portion configured to absorb and retain moisture from the wearer and comprising one or more moisture retention layers, wherein the moisture retention portion comprises a moisture retention portion lateral edge; and
a moisture barrier layer configured to restrict moisture from exiting the moisture retention portion, wherein the one or more moisture retention layers are positioned between the wicking layer and the moisture barrier layer, and wherein the moisture barrier layer comprises a moisture barrier layer lateral edge that is spaced laterally outward from the moisture retention portion lateral edge; and
a plurality of adhesive bonds within the bonded region of the garment, wherein the plurality of adhesive bonds comprises:
an internal peripheral bond positioned on the assembly interior side and that operates to bond the moisture capture assembly to the garment base, and to bond the interior base layer to the wicking layer and to the moisture barrier layer;
an external peripheral bond positioned on the assembly exterior side and that operates to bond the moisture capture assembly to the garment base; and
one or more capture assembly internal bonds that operate to bond the wicking layer to the one or more moisture retention layers, and to bond the moisture barrier layer to the one or more moisture retention layers;
wherein the interior base layer is a closed structure that coincides with the bonded region.

16. The garment of claim 15, wherein the at least one other base layer comprises an intermediate base layer and an exterior base layer, wherein the internal peripheral bond further operates to bond the interior base layer to the intermediate base layer, wherein the intermediate base layer at least partially defines the garment lateral edge, and wherein a base layer lateral outward edge of the exterior base layer is spaced away from the garment lateral edge.

17. The garment of claim 16, wherein the exterior base layer is coextensive with the moisture capture assembly.

18. The garment of claim 15, wherein the one or more moisture retention layers comprises two moisture retention layers positioned between the wicking layer and the moisture barrier layer, and wherein the one or more capture assembly internal bonds further operate to bond the two moisture retention layers to one another.

* * * * *